(12) United States Patent
Beier et al.

(10) Patent No.: US 6,756,492 B1
(45) Date of Patent: Jun. 29, 2004

(54) NUCLEOSIDE DERIVATIVES WITH PHOTO-UNSTABLE PROTECTIVE GROUPS

(75) Inventors: Markus Beier, Heidelberg (DE); Jörg Honeisel, Wiesloch (DE)

(73) Assignee: Deutsches Krebsforschungszentrum Stiftund des Offentlichen Rechts, Heidelberg (DE)

( * ) Notice: Subject to any disclaimer, the term of this patent is extended or adjusted under 35 U.S.C. 154(b) by 0 days.

(21) Appl. No.: 09/958,610

(22) PCT Filed: Apr. 7, 2000

(86) PCT No.: PCT/DE00/01148

§ 371 (c)(1),
(2), (4) Date: Feb. 21, 2002

(87) PCT Pub. No.: WO00/61594

PCT Pub. Date: Oct. 19, 2000

(30) Foreign Application Priority Data

Apr. 8, 1999 (DE) .......................... 199 15 867
Jan. 28, 2000 (DE) .......................... 100 03 631

(51) Int. Cl.[7] .................. C07H 21/00; C07H 21/02; C07H 21/04
(52) U.S. Cl. .................. 536/23.1; 536/24.3; 536/25.3; 536/26.6
(58) Field of Search .................. 536/23.1, 24.3, 536/25.3, 26.6

(56) References Cited

U.S. PATENT DOCUMENTS

| | | | |
|---|---|---|---|
| 5,623,068 A | 4/1997 | Reddy et al. | 536/25.34 |
| 5,753,788 A | 5/1998 | Fodor et al. | 536/22.1 |
| 5,763,599 A | 6/1998 | Pfleiderer et al. | 536/55.3 |
| 5,843,655 A | 12/1998 | McGall | 435/6 |

FOREIGN PATENT DOCUMENTS

| | | |
|---|---|---|
| DE | 36 06 394 A1 | 3/1987 |
| DE | 198 53 242 A1 | 5/2000 |
| DE | 198 58 440 A1 | 6/2000 |
| DE | 199 15 867 A1 | 10/2000 |
| DE | 199 62 803 A1 | 7/2001 |
| DE | 100 03 631 A1 | 8/2001 |
| WO | WO 94/10128 | 5/1994 |
| WO | WO 96/18634 | 6/1996 |
| WO | WO 99/05315 | 2/1999 |

OTHER PUBLICATIONS

Saha, et al., "1,1'–Carbonylbis(3–methylimidazolium) Triflate: An Efficient Reagent for Aminoacylations," *J. Am. Chem. Soc. 111*:4856–4856 (1989).

Fodor, et al. "Light–Directed, Spatially Addressable Parallel Chemical Synthesis," *Science, 251*:767–773 (1991).

Eritja et al., "NPE–Resin, a New Approach to the Sold–Phase Synthesis of Protected Peptides and Oligonucleotides I: Synthesis of the Supports and their Application to Oligonucleotide Synthesis," *Tetrahedron Letters 32*(11):1511–1514 (1991).

Giegrich, et al. "New Photolabile Protecting Groups in Nucleoside and Nucleotide Chemistry—Synthesis, Cleavage Mechanisms and Applications," *Nucleosides and Nucleotides, 17*(9): 1987–1996 (1998).

Himmelsbach, et al., "A versatile new Blocking Group for Phosphate and Aglycone Protection in Nucleosides and Nucleotides," *Tetrahedron 40*(1):59–72 (1984).

McIntyre, "Microfabrication technology for DNA sequencing," *TIBECH 14*:69–73 (1996).

Pirrung and Fallon, "Proofing of Photolithographic DNA Synthesis with 3',5'–Dimethoxybenzoinyloxycarbonyl–Protected Deoxynucleoside Phosphoramidites," *J. Org. Chem. 63*:241–246 (1998).

Schirmeister, et al., "The 2–(4–Nitrophenyl)ethoxylcarbonyl (npeoc) and 2–(2–40–Dinitrophenyl)ethoxycarbonyl (dnpeoc) Groups for Protection Hydroxy Functions in Ribonucleosides and 2'–Deoxyribonucleosides," *Helvetica Chimica Acta 76*:385–401 (1993).

Seliger and Aumann, "Träger–Oligonucleotidsynthese an unvertntzten Copolymeren aus Vinylalkohol un N–Vinylpyrrolidon," *Die Makromolekulare Chemie 176*:609–627 (1975).

Korri–Youssoufi, et al. "Toward Bioelectronics: Specific DNA Recognition Based on an Oligonucleotide–Functionalized Polypyrrole," *IJ. Am. Chem. Soc. 119*:7388–7389 (1997).

Examples

*Primary Examiner*—Jezia Riley
(74) *Attorney, Agent, or Firm*—Albert P. Halluin; Viola T. Kung; Howrey, Simon, Arnold & White, LLP

(57) ABSTRACT

The present invention relates to nucleoside derivatives having photolabile protective groups of general formula (I)

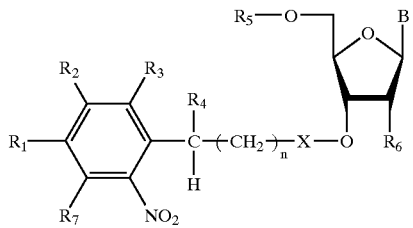

in which

- $R^1$=H, $NO_2$, CN, $OCH_3$, halogen, an alkyl, alkoxy or alkoxyalkyl residue having 1 to 4 C atoms or an optionally substituted aryl residue or an aliphatic acyl residue having 2 to 5 atoms,
- $R^2$=H, $NO_2$, CN, $OCH_3$, halogen, an alkyl, alkoxy or alkoxyalkyl residue having 1 to 4 C atoms or an optionally substituted aryl residue or an aliphatic acyl residue having 2 to 5 atoms,
- $R^3$=H, halogen, $NO_2$, CN, $OCH_3$, an alkyl, alkoxy or alkoxyalkyl residue having 1 to 4 C atoms or an optionally substituted aryl residue or aliphatic acyl residue having 2 to 5 C atoms,
- $R^4$=H, halogen, $NO_2$, CN, $OCH_3$, an alkyl, alkoxy, or alkoxyalkyl residue having 1 to 4 C atoms or an optionally substituted aryl residue or aliphatic acyl residue having 2 to 5 atoms,
- $R^5$=H, dimethoxytrityl or a protective group common in the chemistry of nucleotides or a functional group common for the production of oligonucleotides,
- $R^6$=H, OH, halogen, or $\Psi R^8$, wherein $\Psi$=O or S and $R^8$=alkyl or alkoxyalkyl having 1 to 4 C atoms or an optionally substituted aryl residue or an aliphatic acyl residue having 2 to 5 atoms and a protective group common in the chemistry of nucleotides,
- $R^7$=H, $NO_2$, CN, $OCH_3$, halogen, an alkyl, alkoxy or alkoxyalkyl residue having 1 to 4 C atoms or an optionally substituted aryl residue or aliphatic acyl residue having 2 to 5 atoms,
- n =0 or 1,
- X =$SO_2$, OCO, OCS,
- B=H, adenine, cytosine, guanine, thymine, uracil, 2,6-diaminopurine-9-yl, hypoxanthine-9-yl, 5-methylcytosine-1-yl, 5-amino-4-imidazole carboxylic acid-1-yl or 5-amino-4-imidazole carboxylic acid amide-3-yl, wherein in case B=adenine, cytosine or guanine the primary amino function optionally has a temporary or permanent protective group and/or thymine or uracil optionally has a permanent protective group at the O4 position.

The invention also relates to a method of producing these nucleosides, their use and nucleic acid chips built up therefrom.

8 Claims, 16 Drawing Sheets

Production of the acylation reagent for X = SO₂, OCO, OCS:

alternatively for X = OCO, OCS:

Production of the acylation reagent for X = OCO:

alternatively:

Production of the acylation reagent for X = OCS:

n = 0,1

N-Methylimidazole
CH$_2$Cl$_2$ n = 0,1 alternatively:

n = 0,1 n = 0,1

Production of the acylation reagent for X = SO$_2$:

n = 0,1          n = 0,1

Examples:

Examples

Examples:

I: 19, N-methylimidazole, CH$_2$Cl$_2$
II: trichloroacetic acid, CH$_2$Cl$_2$
III: (2-cyanoethyl)-N,N-diisopropylphosphor imidochloridite, ethyldiisoproylamine, CH$_2$Cl$_2$

Synthesis of DNA chips:

light-controlled
DNA chip synthesis chip synthesis

Detection by hybridization with:
5'-Cy5-d(AAAAAAAAAAAAAAA)

Synthesis of DNA chips:

light-controlled
DNA chip synthesis chip synthesis

Detection by hybridization with:
5'-Cy5-d(AAAAAAAAAAAAAAAA)

Enzymatic reaction on DNA chips:

*Polymerase* (Primer Extension)

5'—TT TTT TTT T—OH 3'

3' AAA AAA AAA ATT ATG CTG AGT GAT ATC 5'

↓ *Polymerase (Klenow-Fragment)*

5'—TT TTT TTT TAA TAC GAC TCA CTA TAG 3'

Cy5- channel chip synthesis (a)

Cy3- channel polymerase (b)

Detection by hybridization with::
(a) 5'-Cy5-d(AAAAAAAAAAAAAAAA)
(b) 5'-Cy3-d(CTATAGTGAGTCGTATTA)

Enzymatic reaction on DNA chips:

*Ligase*

Detection by hybridization with:
(a) 5'-Cy5-d(AAAAAAAAAAAAAAAA)
(b) 5'-Cy3-d(CTATAGTGAGTCGTATTA)

NUCLEOSIDE DERIVATIVES WITH PHOTO-UNSTABLE PROTECTIVE GROUPS

This application is a National Stage of International Application PCT/DE00/01148, filed Apr. 7, 2000; which claims the priority of DE 100 03 631.7, filed Jan. 28, 2000, and DE 199 15 867.3, filed Apr. 8, 1999.

FIELD OF THE INVENTION

The subject matter of the present invention relates to nucleoside derivatives with photolabile protective groups, a method for the production thereof, their use and nucleic acid chips built up therefrom.

BACKGROUND OF THE INVENTION

Photolabile protective groups are of significance for the hydroxy and phosphate functions in nucleosides and/or nucleotides since they are suitable for the light-controlled parallel synthesis of oligonucleotides on a solid support surface (Fodor et al., Science 1991, 251, p. 767 et seq.). It is possible to synthesize therewith oligonucleotides or nucleic acid chips which can be used for sequencing nucleic acids efficiently, for example.

To date, it is only known to produce DNA chips by means of photolithographic methods using 3'-O phosphite amides, which correspondingly carry the temporary photolabile protective group at the 5'-O position (WO-A-96/18634). It is possible to produce DNA chips by means of these nucleic acid building blocks, the oligomer being built up from the 3' end to the 5' end. The finished oligomer is thus anchored to the solid phase via the 3'-O end. The 5'-OH end can be accessed freely. DNA chips which were produced with this method can be used for hybridization experiments but not for certain enzyme reactions (e.g. with DNA polymerase or ligase) which require free 3'-OH.

SUMMARY OF THE INVENTION

It is the object of this invention to provide 3'-photolabile nucleosides and their derivatives and to generate nucleic acid chips using the 3'-photolabile nucleosides obtained therefrom, in which the oligomers built up by light-controlled synthesis are linked to the solid phase via the 5' end and thus enable enzyme reactions at the 3' end.

BRIEF DESCRIPTION OF THE DRAWINGS

(a) production of the acylation reagent in which X=OCO (b) production of the acylation reagent in which X=OCS (c) production of the acylation reagent in which X=$SO_2$

Figure 12:
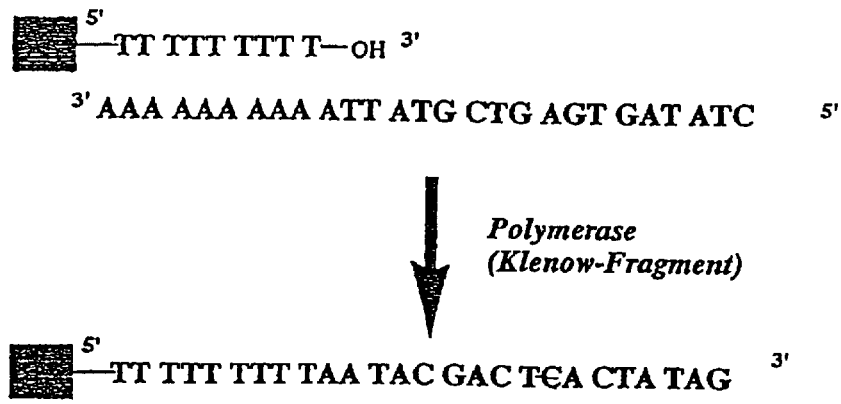
FIG. 12 shows a polymerase reaction on a DNA chip (sequence: $dT_9$) which was produced using 3'-O[2-(2-nitrophenyl)propoxycarbonyl]thymidine-5'-O-[(2-cyanoethyl)-N,N-diisopropyl phosphoramidite]. The polymerase reaction (primer extension) was carried out with the illustrated nucleotide sequences, and the success thereof was made visible by means of hybridization. This figure shows the fluorescence images obtained after simultaneous hybridization with Cy5-labeled $dA_{16}$ and Cy3-labeled d(CTATAGTGAGTCGTA), SEQ ID NO: 3. The $dT_9$ sequence produced by means of light-controlled synthesis on the support surface is detected using Cy5-$dA_{16}$.
Figure 12:
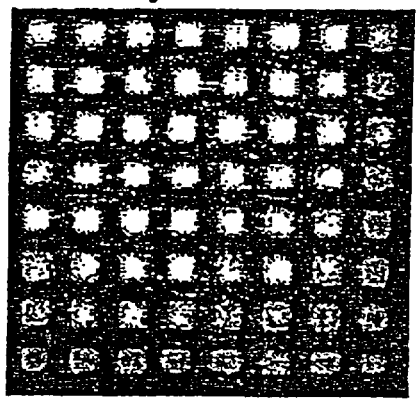
Figure 12:
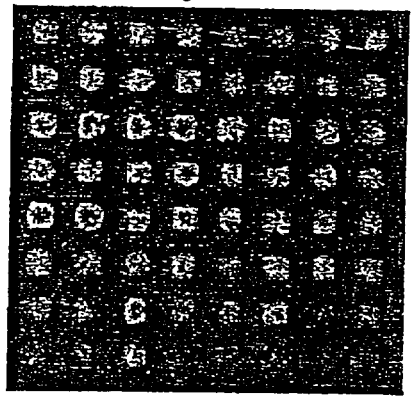

Only the chain extension of the surface-bound primer is detected by the polymerase reaction using Cy-d (CTATAGTGAGTCGTA), SEQ ID NO: 3. Additional sequences in FIG. 12 are identified as SEQ ID NOs: 4–6.

Figure 13:
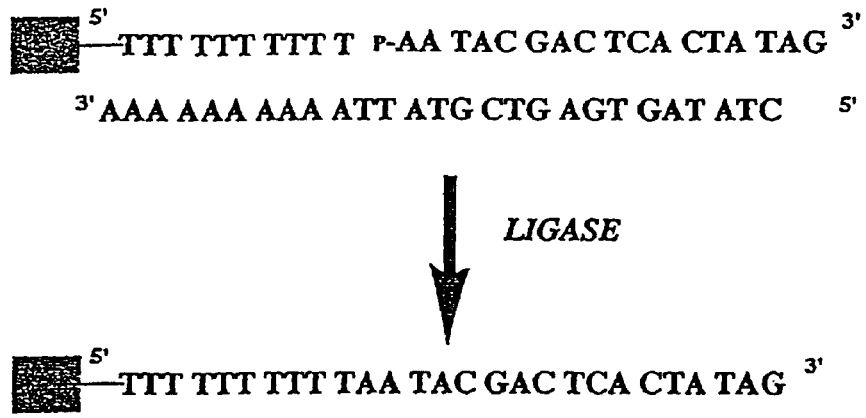
Figure 13:
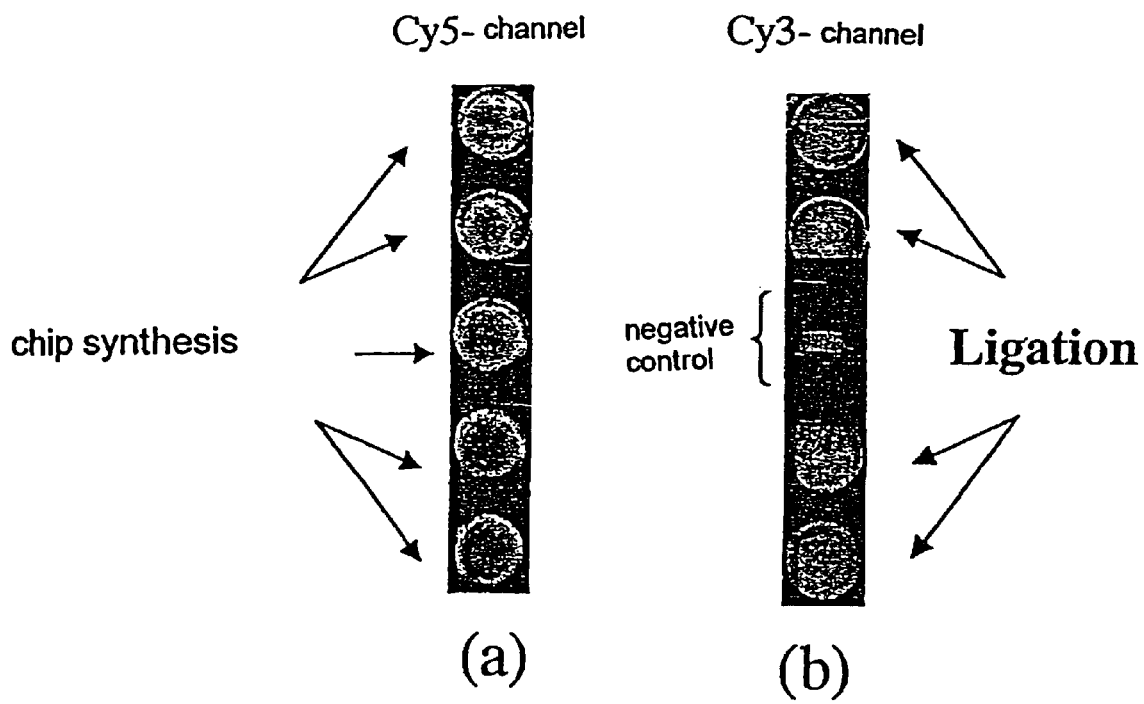

FIG. 13 shows the ligase reaction on a DNA chip (sequence: $dT_{10}$) which was produced using 3'-O-[2-(nitrophenyl)propoxycarboriyl]thymidine-5'-O-[(2-cyanoethyl)-N,N-diisopropyl phosphoramidite). The ligase reaction was carried out using the illustrated nucleotide sequences and its success was made visible by means of hybridization. This figure shows the fluorescence images which were obtained after simultaneous hybridization with Cy5-labeled $dA_{16}$ and Cy3-labeled d(CTATAGTGAGTCGTA), SEQ ID NO: 3. The $dT_{10}$ sequence produced by means of light-controlled synthesis on the support surface is detected by means of Cy5-$dA_{16}$. Only the linkage of the sequence d(5'-phosphate-AATACGACTCACTATAG), SEQ ID NO: 7, is detected with Cy3-d (CTATAGTGAGTCGTA) by the ligase reaction. No ligase reaction was carried out as negative control in the middle of the arrays, and therefore this spot is also only visible in the Cy5 channel but not in the Cy3 channel. Additional sequence in FIG. 13 is identified as SEQ ID No: 8.

DETAILED DESCRIPTION OF THE INVENTION

This object is achieved according to the invention by the nucleoside derivatives of general formula (1) according to claim 1. Advantageous embodiments follow from the subclaims.

Nucleoside derivatives according to the invention comprise the following fornula:

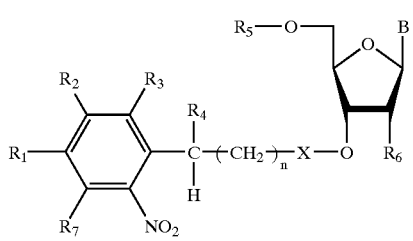

wherein

- $R^1$=H, $NO_2$, CN, $OCH_3$, halogen, an alkyl, alkoxy or alkoxyalkyl residue having 1 to 4 C atoms or an optionally substituted aryl residue or an aliphatic acyl residue having 2 to 5 atoms,
- $R^2$=H, $NO_2$, CN, $OCH_3$, halogen, an alky, alkoxy or alkoxyalkyl residue having 1 to 4 C atoms or an optionally substituted aryl residue or an aliphatic acyl residue having 2 to 5 atoms,
- $R^3$=H, halogen, $NO_2$, CN, $OCH_3$, an alky, alkoxy or alkoxyalkyl residue having 1 to 4 C atoms or an optionally substituted aryl residue or aliphatic acyl residue having 2 to 5 atoms,
- $R^4$=H, halogen, $NO_2$, CN, $OCH_3$, alkyl, alkoxy or alkoxyalkyl residue having 1 to 4 C atoms or an optionally substituted aryl residue or aliphatic acyl residue having 2 to 5 atoms,
- $R^5$=H, dimethoxytrityl or a protective group common in the chemistry of nucleotides or a functional group common for the production of oligonucleotides,
- $R^6$=H, OH, halogen or $\Psi R^8$, in which $\Psi$=O or S and $R^8$=alkyl or alkoxyalkyl having 1 to 4 C atoms or an optionally substituted aryl residue or an aliphatic acyl residue having 2 to 5 atoms and a protective group common in the chemistry of nucleotides,
- $R^7$=H, $NO_2$, CN, $OCH_3$, halogen, an alkyl, alkoxy or alkoxyalkyl residue having 1 to 4 C atoms or an optionally substituted aryl residue or aliphatic acyl residue having 2 to 5 atoms,
- n=0 or 1,
- X=$SO_2$, OCO, OCS,
- B=H, adenine, cytosine, guanine, thymine, uracil, 2,6-diaminopurine-9-yl, hypoxanthine-9-yl, 5-methylcytosine-1-yl, 5-aniino-4-imidazole carboxylic acid-1-yl or 5-amino-4-imidazolecarboxylic amide-3-yl, wherein in case B=adenine, cytosine or guanine the primary amino function optionally has a temporary or permanent protective group and/or thymine or uracil optionally has a permanent protective group at the O4 position.

The alkyl, alkoxy or alkoxyalkyl group of residues $R^1$, $R^2$, $R^3$, $R^4$ and $R^7$ may be linear or branched, substituted (in particular with one or more halogen atoms) or unsubstituted and saturated or unsaturated. A bridge-type bond may exist between the residues, e.g. via a methylene group, so that another ring function results. This applies analogously to the acyl or aryl group of residues $R^2$, $R^3$, $R^4$ or $R^7$. Here, alkyl groups along with halogen atoms are in consideration as substituents. Preferred alkyl residues are methyl, ethyl, n-propyl, n-butyl, iso-propyl, or tert-butyl groups. Preferred alkoxy residues are the methoxy, ethoxy or tert-butoxy grouping. Preferred aliphatic acyl residues are the formyl residue (—CHO), acetyl residue (—CO—$CH_3$), propionyl residue (—CO—$C_2H_5$) or butyryl residue (—CO—$C_3H_7$).

Preferred (hetero)aryl residues are the phenyl, thienyl, thiophenyl, furyl, furanyl, pyranyl, pyrrolyl, imidazolyl, pyrazolyl, pyridyl, pyrazinyl, pyrimidinyl, pyrazinyl, pyridazinyl, thiazolyl, oxazolyl, indolyl, pyrrolinyl, imidazolinyl, pyrazolinyl, thiazolinyl, triazolyl, or tetrazolyl group and annelated rings resulting therefrom.

$R^4$ preferably represents H or a methyl residue. When $R^4 \neq H$, substituents $R^1$ to $R^3$ at the phenyl ring are preferably hydrogen residues, and when $R^2$=$OCH_3$, $R^3$ is preferably a hydrogen residue.

At the $R^5$ position, "a protective group common for the production of oligonucleotides" is e.g. a phosphite amide group, such as p-NC—$CH_2$—$CH_2$—O—P—$N(Q)_2$, p-NC—$C_6H_4$—$CH_2$—$CH_2$—O—P—$N(Q)_2$, p-$NO_2$—$C_6H_4$—$CH_2$—$CH_2$—O—P—$N(Q)_2$ or $CH_2$=CH—$CH_2$—O—P—$N(Q)_2$, in which the Q groups maybe equal or different and stand for linear or branched alkyl residues having 1 to 4 C atoms, preferably ethyl or isopropyl residues.

At the $R^6$ position, "a protective group common in the chemistry of nucleotides" (=$R^8$) represents in particular H and the common O-alkyl, O-alkenyl, O-acetal or O-silylether protective groups.

Preferred protective groups are O-methyl or O-ethyl residues, O-allyl residues, O-tetrahydropyranyl or O-methoxytetrahydropyranyl residues and O-t-butyl dimethylsilyl residues.

The protective groups optionally occurring permanently at the bases B are preferably based on acyl protective groups. The preferred groups are above all phenoxyacetyl, tert-butyl phenoxyacetyl, isobuyryl, acetyl, benzoyl, allyloxycarbonyl, phthaloyl, dansylethyloxycarbonyl, 2-(4-nitrophenyl)ethoxycarbonyl or dimethylformamidino residues. In the case of adenine, cytosine and guanine, phenoxyacetyl, tert-butylphenoxyacetyl, acetyl or 2-(4-nitrophenyl)ethoxycarbonyl groups are preferred for the protection of the exocyclic amino functions. The $O^6$ position of guanine can optionally be protected by a protective group such as 2-(4-nitrophenylsulfonyl)ethyl or 2-(4-nitrophenyl) ethyl. Likewise the $O^4$ position of thymine or uracil may have a protective group such as 2-(4-nitrophenylsulfonyl) ethyl or 2-(4-nitrophenyl)ethyl.

According to the invention halogen is F, Cl, Br, or I, the last three elements being preferred.

Figure 2:
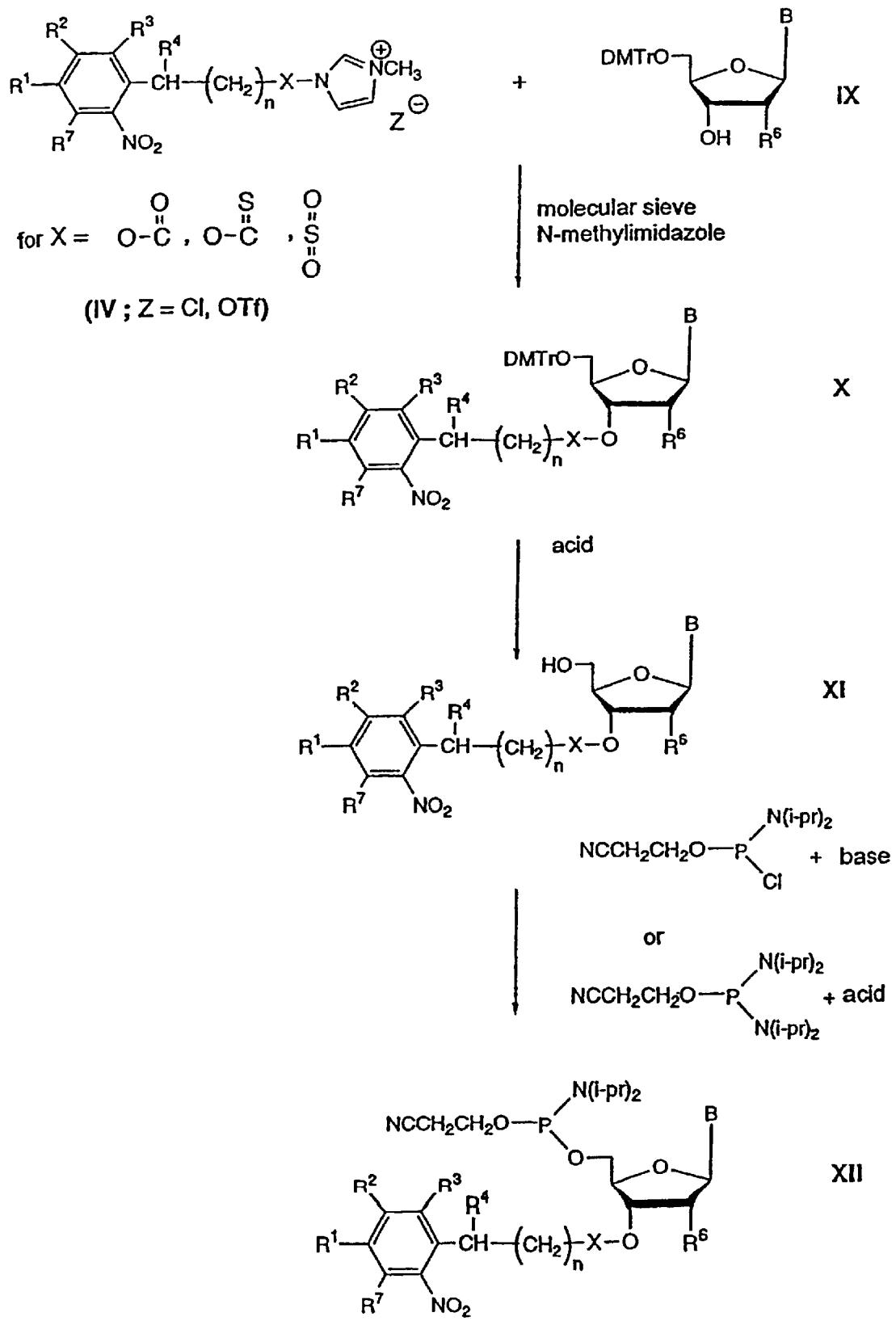
FIG. 2: general synthesis diagram of 3'-photolabile nucleoside derivatives according to the invention

The production of the nucleoside derivatives according to the invention is shown in FIG. 2 by way of example, and reference is made thereto below. The mention of certain halogen and alkyl substitutions always comprises equivalents having equal effects, e.g. "chloro-" does not rule out that the corresponding iodine or bromine compounds can be used as well. This applies likewise to "methyl" which also includes the corresponding other lower alkyl compounds, such as ethyl, propyl or butyl. Residues $R^1$, $R^2$, $R^3$, $R^4$, $R^6$, $R^7$ and X are as defined above.

Figure 1:
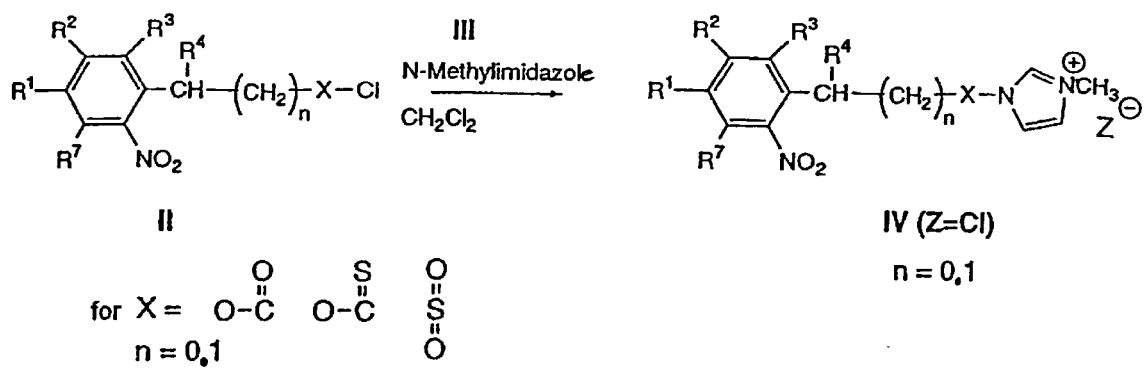
FIG. 1: production of an acylating reagent (general)
Figure 1:
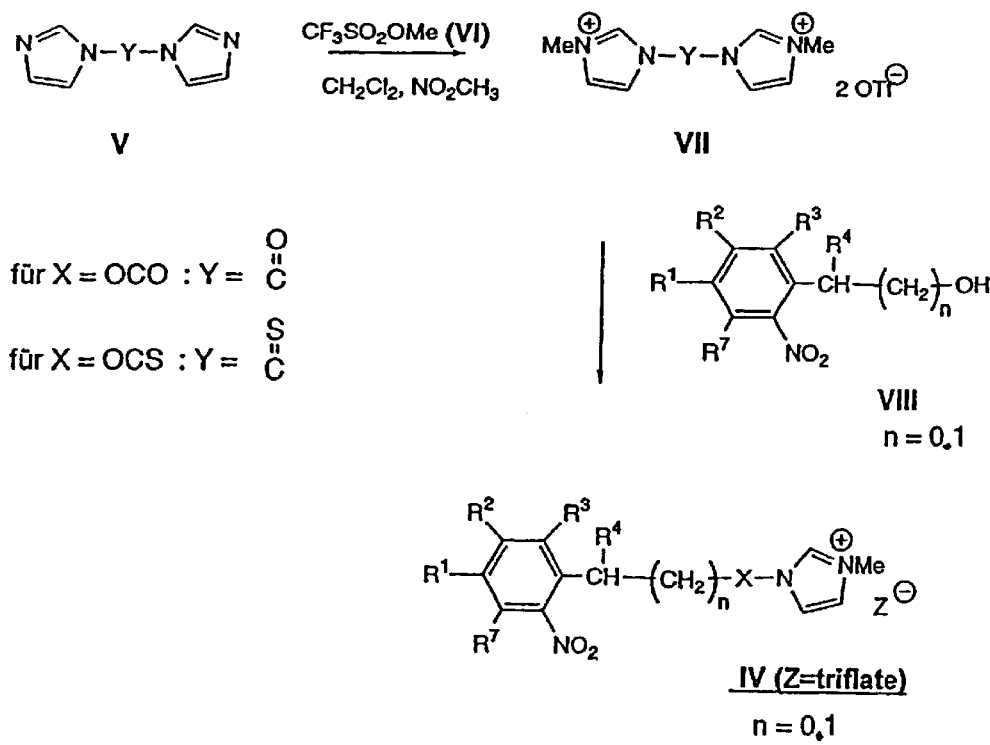
Figure 1A:
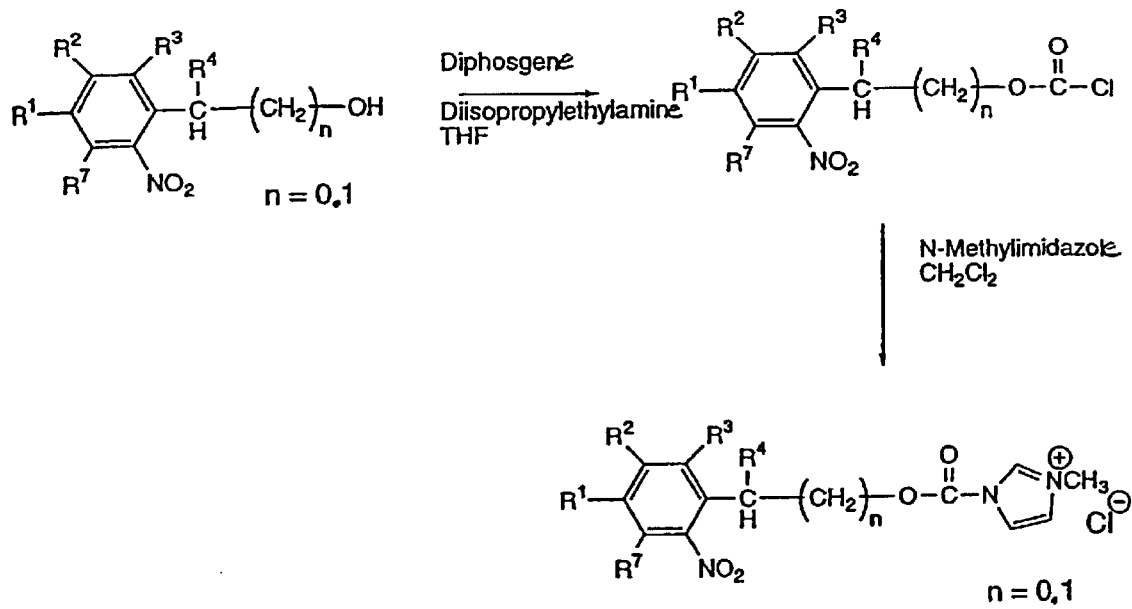
Figure 1A:
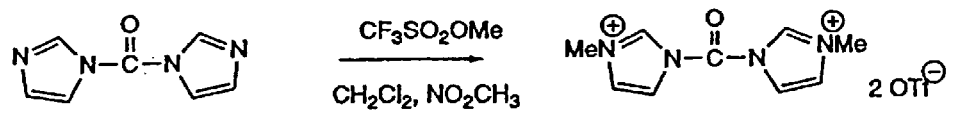
Figure 1A:
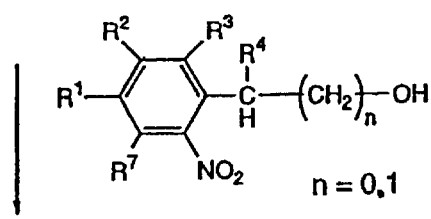
Figure 1A:
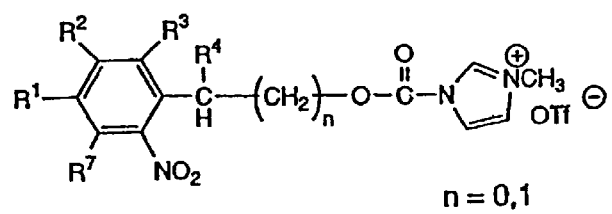
Figure 1B:
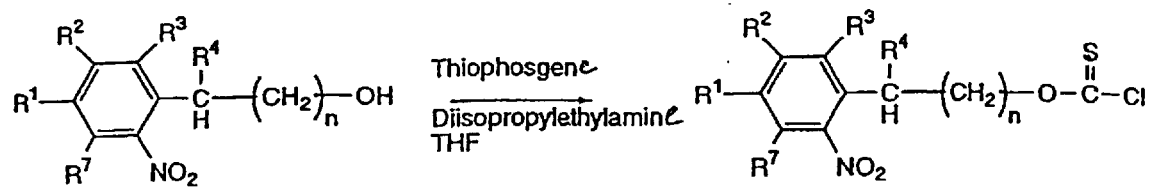
Figure 1B:
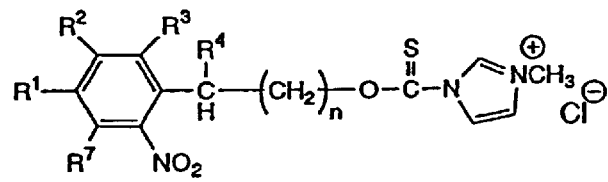
Figure 1B:
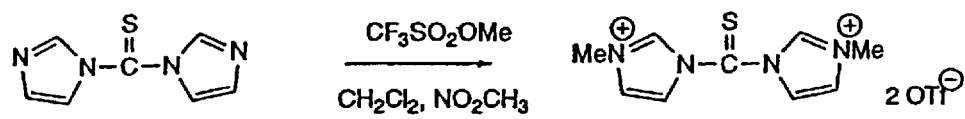
Figure 1B:
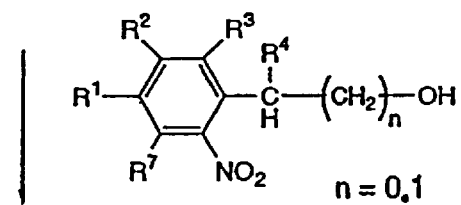
Figure 1B:
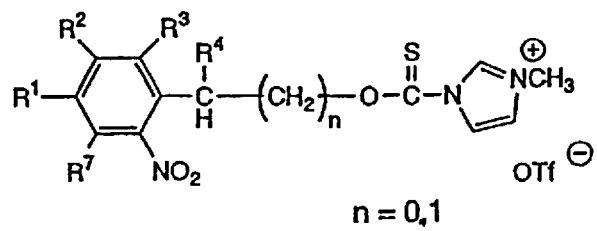
Figure 1C:
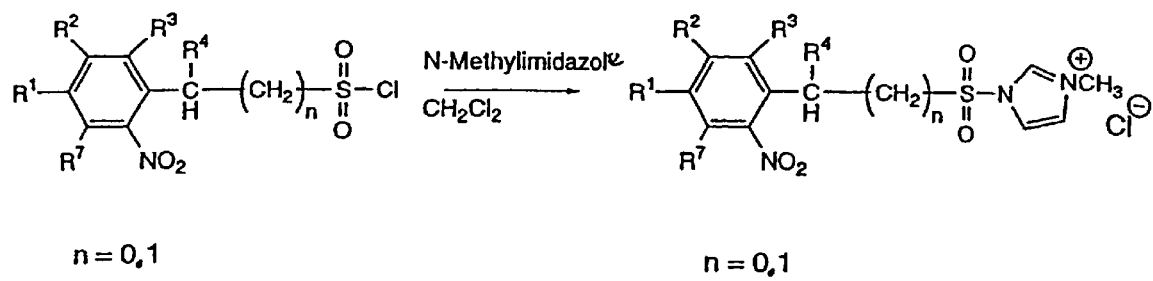

Production begins with the preparation of an acylation reagent. In this connection, reference is made to FIG. 1. For this, a chlorocarbonic ester (II, wherein X=OCO), is preferably used as a basis. It can be obtained according to the specification of WO-A-96/18634 or according to below Example 1, for example. Correspondingly, a desired chlorothiocarbonic ester (II, wherein X=OCS) is available via an analogous reaction using thiophosgene. The acylation reagent (IV) is then generated by reacting the chlorocarbonic ester (II, wherein X=OCO) or the chlorothiocarbonic ester (II, wherein X=OCX) or a corresponding sulfonylchloride derivative (II, X=$SO_2$) with a compound (III), preferably N-methylimidazole. These reactions are carried out in a polar organic solvent, preferably dichloromethane, at temperatures between −10° C. and +10° C., preferably at 0° C. It is preferred to add molecular sieve to the reaction which is carried out using compound (III), preferably N-methylimidazole, in excess with regard to the compound (II) used: 1–10 equivalents, preferably 2–5 equivalents. As an alternative to N-methylimidazole, the acylation reagent may also be generated by means of other heterocyclic compounds (III), such as pyridine, 4-N,N-dimethylaminopyridine (DMAP), triazole, tetrazole or imidazole.

Based on N-N-carbonyldiimidazole (V, Y=CO) or N-N-thiocarbonyl diimidazole (V, Y=CS) the acylation reagent (IV; Z=triflate) is alternatively available following methylation with a methylation reagent (VI), preferably trifluoromethane sulfonic acid methyl ester, and reaction with the corresponding alcohol (VIII). In this case, the reaction is carried out preferably in a polar organic solvent, preferably in nitromethane or a mixture of nitromethane and dichloromethane, at temperatures between −10 and +10° C., preferably at 0° C. The methylation of(V) is carried out e.g. according to Rapoport et al., J. Am. Chem. Soc. 1989, 111, pp. 4856–4859. Having completed methylation, the corresponding alcohol (VIII) is added and the imidazolium-type acylating agent (IV; Z=triflate) is thus generated in the form of a triflate salt. If methyl iodide or Meerwein salts are used for the methylation of (V) as methylation reagent (VI), the acylation reagents (IV) can be generated correspondingly in the form of their iodide or tetrafluoroborate salts. It is preferred to react compounds (V) with the corresponding methylation agent in the ratio of 1:1 to 1:10, the ratio of 1:2 being preferred. It is also preferred to react the methylated form (VI) with the corresponding alcohol (VIII) in the ratio of 1:1 to 1:10, more preferably in the ratio of 1:1 to 1:2.

The acylation reagent (IV) is further reacted with an optionally protected nucleoside (IX). 5'-DMTr-protected nucleosides of general formula (IX) can be purchased from the companies of Proligo, Fluka, Sigma or Aldrich, for example.

The acylation reagent (IV) is reacted with the protected nucleosides (IX) preferably in dichloromethane or a solvent mixture of dichloromethane and a polar organic solvent, optionally in the presence of a base, such as pyridine, N-methylimidazole, 4-N,N-dimethylaminopyridine, ethyldiisopropylamine (EtN(i-pr)$_2$) or triethylamine, at temperatures between −60 and +25° C., preferably at 0° C. It is preferred to use dichloroethane, nitromethane, DMF or pyridine as a polar organic solvent. The mixing ratio between dichloromethane and polar organic solvent is not subject to limitation. However, 1 to 3 parts by volume of dichloromethane per part by volume of polar organic solvent are preferred. A solution of the acylation reagent (IV) in dichloromethane is charged by preference and the nucleoside (IX) which was also dissolved in dichloromethane is added dropwise. The molar ratio of acylation reagent to nucleoside may be preferably between 1:1 and 5:1, preferably at 3:1, most preferably at 2:1, i.e. the acylation reagent is used by preference in excess. The concentration of the nucleoside in the solvent mixture is not subject to limitation. However, it ranges preferably from 0.1 to 3.0 mmol per 10 ml solvent.

Having carried out the conversion (preferable reaction time: 1–12 hours), the resulting nucleoside derivative (X) can be isolated. The 5'-protective group at the nucleoside constituent is then cleaved by reacting preferably trichloroacetic acid or toluenesulfonic acid optionally with camphorsulfonic acid or dichloroacetic acid in dichloromethane. The nucleoside derivative (XI) is obtained which follows formula (I).

If desired, a phosphite amide group can be introduced at the 5' position of the nucleoside derivative (XI). This is done e.g. by reacting the nucleoside derivative (XI) with bis (diisopropylamino)(β-cyanoethyoxy)phosphine by adding a slightly acidic catalyst (e.g. tetrazole, pyridine hydrochloride) or by reacting the nucleoside derivative with chloro-diisopropylamino-2-cyanoethoxy)phosphine by adding a base (e.g. diisopropylethylamine, N-methylmorphine, lutidine or collidine) and a solvent (e.g. THF, dichloromethane). In this case, compound (XII) forms.

The advantage of carrying out the reaction of the protected nucleoside with a mild acylation reagent is in the selectivity of the reaction. Quantitative acylations of the 3'-O position of the nucleoside building block are obtained without the formation of disadvantageous byproducts. If more reactive acylation reagents, such as the corresponding chlorocarbonic ester itself, are used for this purpose, an uncontrolled reaction will occur. A large number of byproducts form, i.e. there is no selectivity for the desired 3-monoacylated product. In a particularly preferred embodiment the protected nucleoside is carried out with the acylation reagent by adding molecular sieve. An increase in the selectivity for the desired 3-monoacylated product can be observed when molecular sieve is used.

The 3'-photolabile nucleosides according to the invention can be used for the photolithographic nucleic acid chip synthesis. A person skilled in the art is sufficiently familiar with methods for this (e.g. Fodor et al., supra). A suitable method for this purpose is also described in German application DE 198 58 440.7, for example. Although this application describes a method which starts from 5'-photolabile nucleosides, it is possible to analogously apply the method indicated therein to the use of 3'-photolabile 5'-phosphite amides (according to formula XII of FIG. 2). The irradiation step of this method, which is common for the chip synthesis, is carried out in the presence of a base. The advantage of this method for photolithographic biochip synthesis is that there is efficient cleavage of photolabile protective groups.

According to the invention a nucleic acid chip is understood to mean biomolecules, such as DNA or RNA, and nucleic acid analogs, such as PNA, LNA or chimeras thereof, all built up on a support, with DNA, RNA or among one another.

According to the invention any support or matrix common in this field can be used for the production of nucleic acid chips. This group comprises in particular glass, sheets or membranes made of polypropylene, nylon, cellulose, cellulose derivatives (e.g. cellulose acetate, cellulose mixed ester), polyethersulfones, polyamides, polyvinyl chloride, polyvinylidene fluoride, polyester, teflon or polyethylene. The support surfaces may also be provided with free or protected functional groups, e.g. an amino group, hydroxyl group, carboxyl group, carbonyl group, thiol, amide or phosphate group. In a preferred embodiment, the support surfaces show derivatization according to German patent application 198 53 242.3.

In the above-mentioned preferred method of synthesizing photolithographic biochips according to German application DE 198 5 8 440.7, the steps of condensation, oxidation and capping are carried out as usual (Fodor et al., Science, 1991, 251, p. 767 et seq.). However, the first step of synthesis, namely the irradiation, takes place by adding bases, preferably strong bases, in particular non-nucleophilic bases, which in co-operation with the light used for the irradiation results in a surprisingly effective cleavage of the protective groups. The bases with which the person skilled in the art is familiar, such as DBU (1,8-diazabicyclo[5.4.0]undec-7-ene, DBN (1,5-diazabicyclo-[4.3.0]non-5-ene, diisopropylethylamine, pyridine, piperidine, triethylamine, diisopropylamine, N-methylmorpholine, 2,6-lutidine, collidine, N-methylimidazole, dabco, N,N-dimetheylaminopyiridine, are suitable bases. The irradiation can be carried out under common conditions. The wavelength of irradiation depends on the protective group used. The suitable wavelengths are known to the person skilled in the art. The amount of base present during the irradiation varies between 0.01 M and 1.0 M and depends, of course, on the basicity. It has proved successful to use 0.03 to 1 M (preferably 0.05 to 0.5 M) DBU in acetonitrile, 0.03 to 0.8 M (preferably 0.05 M) diisopropylethylamine in acetonitrile or 0.03 to 1 M (preferably 0.05 M) piperidine in acetonitrile.

Figure 3:
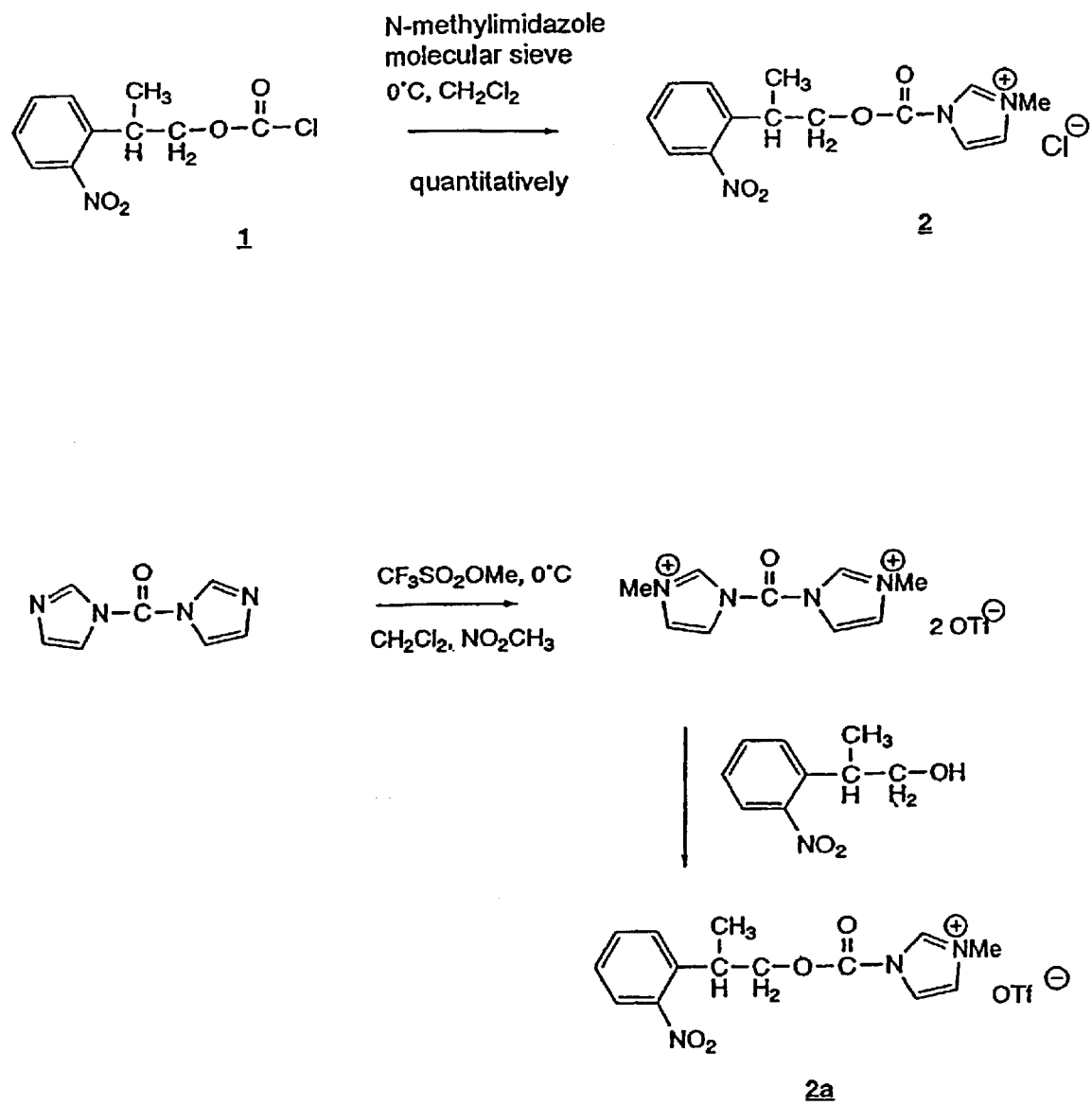
FIGS. 3–7: synthesis diagrams of the compounds according to Examples 1–16
Figure 4:
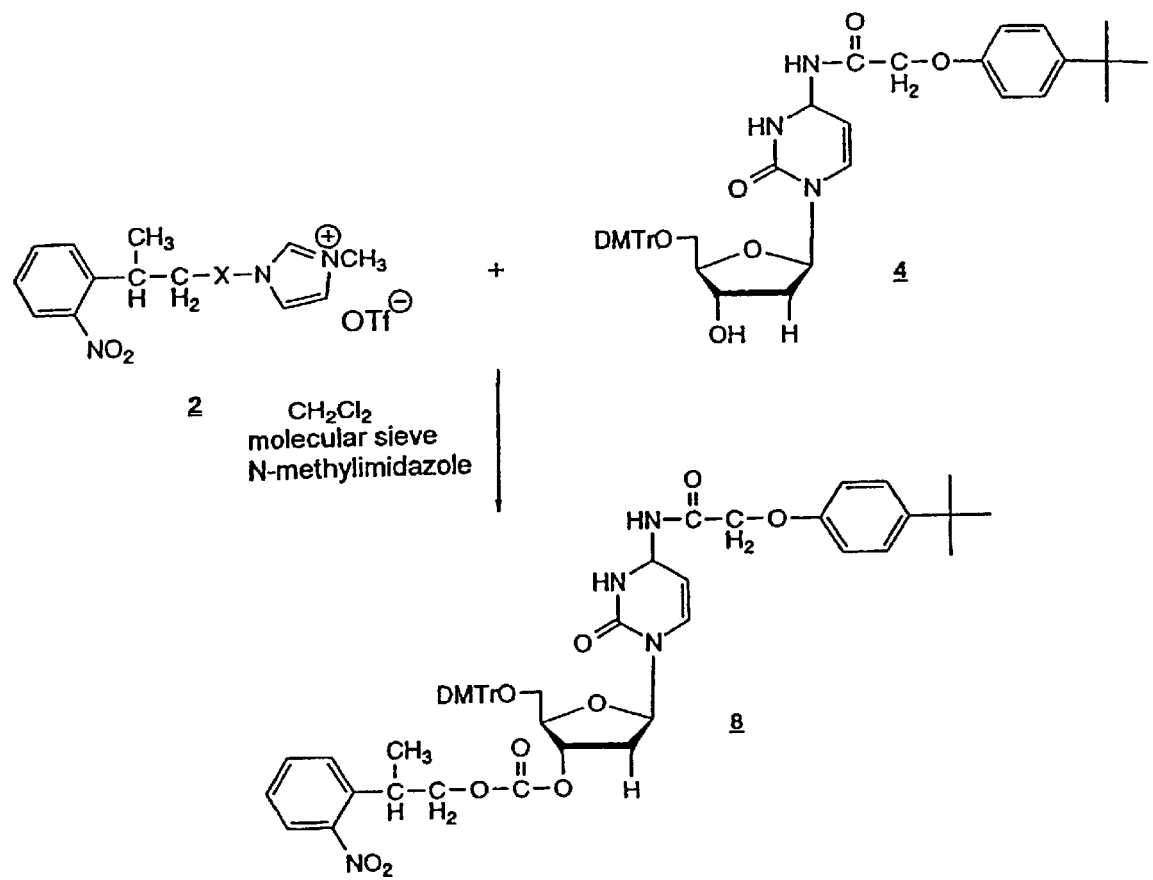
Figure 5:
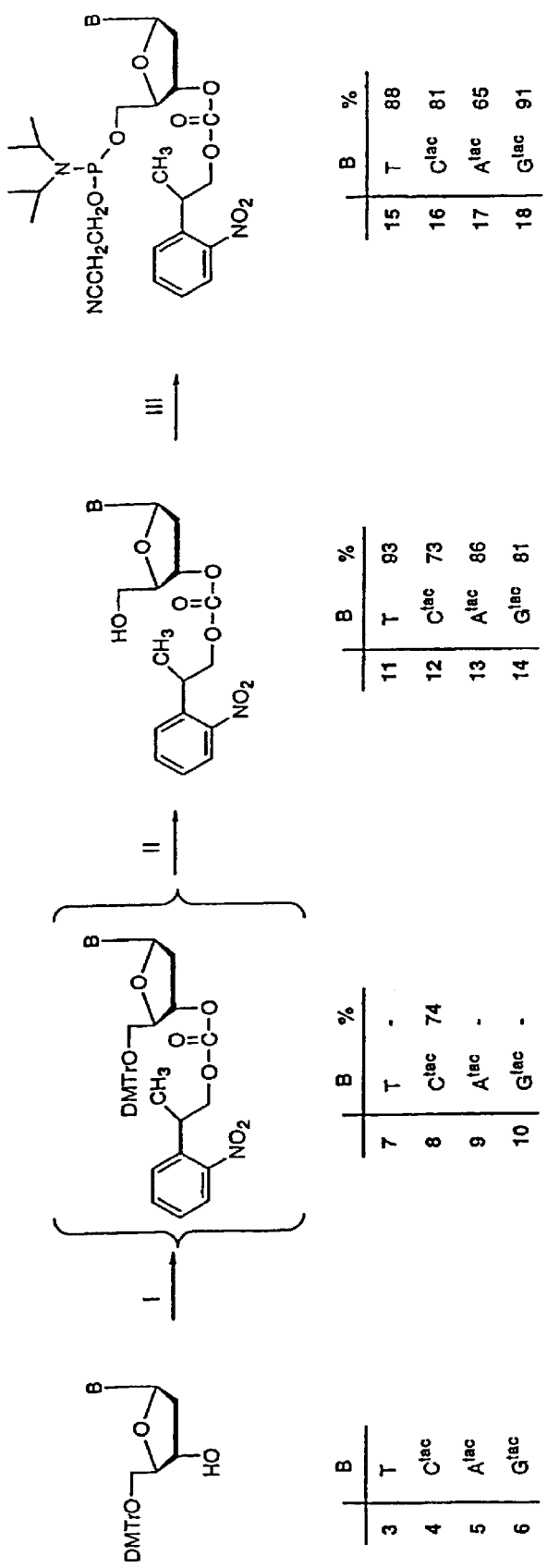
Figure 6:
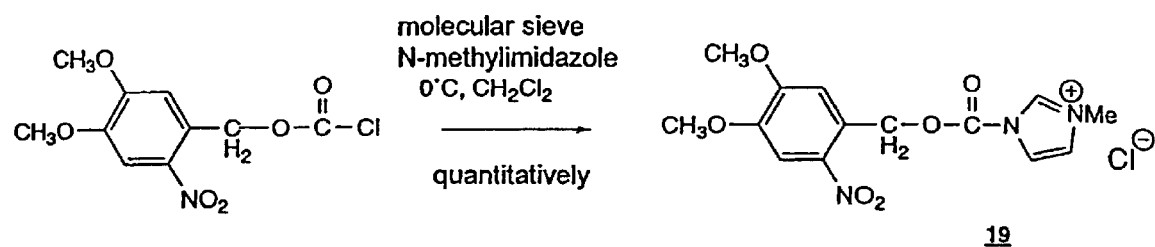
Figure 7:
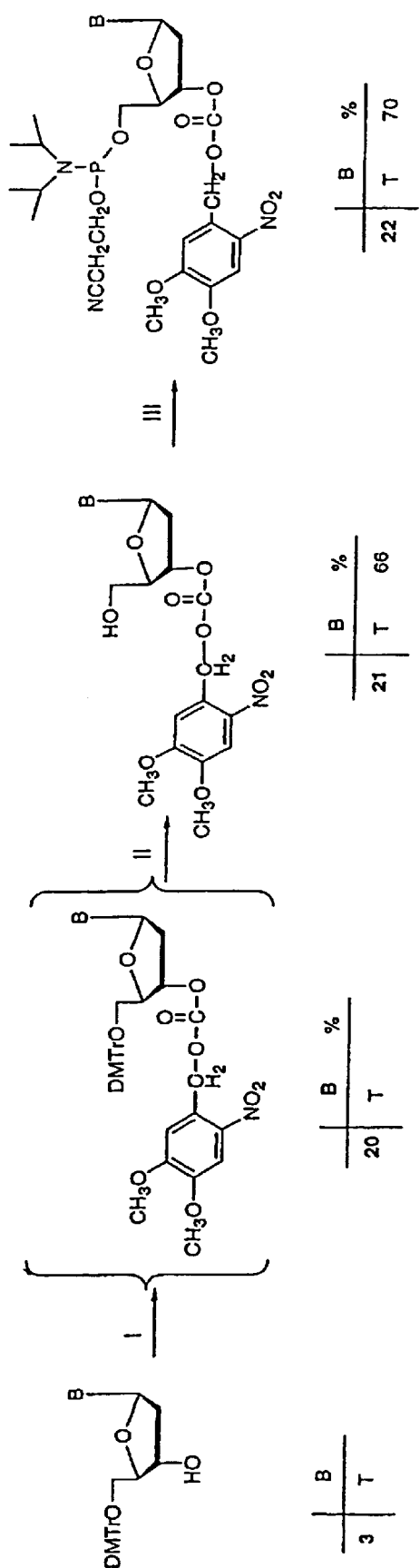

Nucleic acid chips produced using nucleosides according to the invention are characterized in that the finished oligomer is bound with the solid phase via the 5' position whereas the 3'-OH is freely accessible (cf. FIG. 3). DNA chips produced using this method can be used for both hybridization experiments and certain enzyme reactions (e.g. DNA polymerase) which require free 3'-OH. Thus, nucleic acid chips (preferably DNA chips) which were produced using this strategy have a much wider field of application, since it is possible to carry out all experiments therewith—likewise to "common" DNA chips—and also highly parallel solid phase-supported enzyme reactions (e.g. cDNA synthesis, ligase reactions, reverse transcription, PCR, multiplex PCR). This opens up new fields of application (e.g. DNA computing, solid phase-supported sequencing).

EXAMPLES

The invention is described in more detail by means of the below examples.

The reaction schemes for the production of the following compounds is shown in FIGS. 3 to 7, to which reference is made below.

Reagents: DMTr-protected nucleosides, 2-cyanoethyl-N,N,N,N-tetraisopropyl-phosphoro-diamidite and 2-cyanoethyl-N,N-diisopropylphosphoro-imidochloridite were purchased from Proligo (Hamburg, Germany). All the other reagents were obtained from Fluka (Ulm, Germany).

Example 1

2-(2-nitrophenyl)propoxycarbonylchloride (1)

A solution consisting of 7.2 g 2-(2-nitrophenyl)propanol (39.7 mmol) and 4.4 ml N-methylmorpholine (39.7 mmol) in 15 ml absolute THF are slowly added to 5 ml diphosgene (41.4 mmol) in 10 ml absolute THF at 0° C. in a nitrogen atmosphere through a needle. Having stirred for 1 hour at 0° C., some of the precipitate is sucked off and the filtrate is withdrawn at the high vacuum. 6.91 g of (1) is obtained in the form of a brown oil (71%).

Example 2

$N^3$-[2-(2-nitrophenyl)propoxycarbonyl]-N-methyl imidazolium chloride (2)

1.07 ml 2-(2-nitrophenyl)propoxycarbonyl chloride (1) (4.4 mmol) are slowly added dropwise to a solution of 1.24 ml N-methylimidazole (14.7 mmol) in 40 ml dichloromethane at 0° C. over molecular sieve 4 Å. Following stirring for 30 minutes in an ice bath this solution is used directly for acylation with 1.2 equivalents of the 5'-O-protected nucleoside building blocks.

Example 3

1-methyl-3-[2-(2-nitrophenyl)propoxycarbonyl] imidazolium triflate (2a).

2.19 g N,N-carbonyldiimidazole (13.5 mmol) are dissolved in 40 ml absolute dichloromethane and 10 ml absolute nitromethane in a nitrogen atmosphere and cooled to 0° C. 3 ml trifluoromethanesulfonic acid methyl ester (27 mmol) are added and stirred at 0° C. After 30 minutes, a solution consisting of 1.22 g 2-(2-nitrophenyl)propanol (6.75 mmol) in 10 ml absolute dichloromethane are added. After a reaction time of 1 hour, the reaction solution can be used directly for acylation with 1.2 equivalents of the 5'-O-protected nucleoside building blocks.

Example 4

N4-((4-$^{tert}$butylphenoxy)acetyl)-5'-O-(4,4'-dimetboxytrityl)3'-O-[2-(2-nitrophenyl) propoxycarbonyl]-2'-deoxycytidine (8)

A solution of 2.27 g N4-((4-$^{tert}$butylphenoxy)acetyl)-5'-O-(4,4'-dimethoxytrityl)-2'-O-deoxycytidine (4) (3.1 mmol) in 20 ml dichloromethane is added dropwise at 0° C. to 1.2 equiv $N^3$-[2-(2-nitrophenyl)propoxycarbonyl]-N-methylimidazolium chloride (2) (3.7 mmol) in 50 ml dichloromethane through a molecular sieve 4 Å within 10 minutes. The reaction mixture was stirred at 0° C. overnight, then extracted using saturated NaHCO$_3$ (100 ml), dried via Na$_2$SO$_4$, and evaporated. Purification via flash chromatography (0–66% ethyl acetate in toluene) yielded 2.12 g (74%) of the title compound.

$^1$H-NMR (DMSO): δ 10.90 (br, NH), 8.04 (2d, H—C(6)), 7.80 (m, 1H o ad NO$_2$), 7.67 (m, 1H m ad NO$_2$, 1H p ad NO$_2$), 7.47 (m, 1H m ad NO$_2$), 7.19–7.34 (m, 9H DMTr, 2H m ad $^{tert}$butyl), 6.99 (2d, H—C(5)), 6.84 (n, 4 H DMTr, 2H o ad $^{tert}$butyl), 6.07 (m, H—C(1')), 5.10 (m, H—C(3')), 4.77 (s, CH$_2$O), 4.14–4.35 (m, OCH$_2$CH, H—C(4')), 3.70 (m, 2 OCH$_3$), 3.51 (m, CHCH$_3$), 3.20–3.30 (m, 2 H—C(5')), 2.51 (m, H—C(2')), 2.31 (m, H—C(2')), 1.28 (d, CHCH$_3$), 1.24 (s, C(CH$_3$)$_3$). HRMS (FAB, M+H$^+$) calculated for C$_{52}$H$_{54}$N$_4$O$_{12}$: 927.3816. Found: 927.3926. ESI-MS: 927 (M+H$^+$), 950 (M+Na$^+$). R$_f$(toluene/ethyl acetate 2:1) 0.34

Example 5

N4-((4-$^{tert}$butylphenoxy)acetyl-5'-O-(4,4'-dimethoxytrityl)-3'-O-[2-(2-nitrophenyl) propoxycarbonyl]-2'-deoxycytidine (8)

A solution of 1.68 g N4-((4-$^{tert}$butylphenoxy)acetyl)-5'-O-(4,4'-dimethoxytrityl)-2'-O-deoxycytidine (4) (2.3 mmol) in 10 ml dichloromethane is added dropwise at 0° C. to 1.2 equiv 1-methyl-3-[2-(2-nitrophenyl)propoxycarbonyl] imidazolium triflate (2a) (2.8 mmol) in 8 ml dichloromethane and 2 ml nitromethane through a molecular sieve 4 Å within 10 minutes. The reaction mixture was stirred at 0° C. overnight, then extracted using saturated NaHCO$_3$ (100 ml), dried via Na$_2$SO$_4$ and evaporated. The title compound is purified via flash chromatography (0–66% ethyl acetate in toluene). R$_f$ (toluene/ethyl acetate 2:1) 0.34

Example 6

3'-O-[2-(2-nitrophenyl)propoxycarbonyl]thymidine (11)

A solution of 2 g 5'-O-(4,4'-dimethoxytrityl)thymidine (3) (3.67 mmol) in 20 ml dichloromethane is added dropwise at 0° C. to 1.2 equiv $N^3$-[2-(2-nitrophenyl)propoxycarbonyl]-N-methylimidazolium chloride (2) (4.4 mmol) in 30 ml dichloromethane through a molecular sieve 4 Å within 10 minutes. The reaction mixture was stirred at 0° C. overnight, then extracted using 0.5% HCl (100 ml), dried via Na$_2$SO$_4$ and evaporated. 10% trichloroacetic acid (70 ml) in dichloromethane is added to the organic phase and stirred for 2 minutes. Thereafter, the deep-red solution is extracted twice using saturated NaHCO₃ (100 ml), dried via Na₂SO₄ and evaporated. Purification via flash chromatography (0–10% methanol in toluene/ethyl acetate (5:4)) yielded 1.53 g (93%) of the title compound.

$^1$H-NMR (DMSO): δ_11.26 (br, NH), 7.82 (m, 1H o ad NO₂), 7.69 (m, H—C(6), 1H m ad NO₂, 1H p ad NO₂), 7.49 (m, 1H m ad NO₂), 6.11 (m, H—C(1')), 5.09 (m, H—C(3')), HO—C(5')), 4.33 (m, CHCH₂O), 3.96 (m, H—C(4')), 3.59 (2m, 2 H—C(5')), 3.52 (m, CHCH₂O), 2.24 (m, 2 H—C (2')), 1.77 (2s, CH₃), 1.29 (d, CHCH₃). HRMS (FAB, M+H⁺) calculated for C₂₀H₂₃N₃O₉: 450.1512. Found: 450.1524. ESI-MS: 450 (M+H⁺), 472 (M+Na⁺), 899 (2M+H⁺), 921 (2M+Na⁺). R$_f$ (toluene/ethyl acetate 1:2) 0.21

Example 7

N4-((4-$^{tert}$butylphenoxy)acetyl)-3'-O-[2-(2-nitrophenyl)propoxycarbonyl]-2'-deoxycytidine (12)

As described for 11 with N4-((4-$^{tert}$butylphenoxy)acetyl)-2'-deoxycytidine (4) (5 g, 6.93 mmol) in 50 ml dichloromethane and 2 (2.71 g, 8.32 mmol) in 50 ml dichloromethane. Purification by precipitation using toluene yielded 3.16 g (73%) of the title compound.

$^1$H-NMR (DMSO): δ_10.87 (br, NH), 8.29 (d, H—C(6)), 7.82 (m, 1H o ad NO₂), 7.69(m, 1H m ad NO₂, 1H p ad NO₂), 7.48 (m, 1H m ad NO₂), 7.29 (m, 2H m ad $^{tert}$butyl), 7.13 (d, H—C(5)), 6.84 (m, 2H o ad $^{tert}$butyl), 6.08 (m, H—C(1')), 5.10 (m, H—C(3')), HO—C(5')), 4.77 (s, CH₂O), 4.33 (m, OCH₂CH), 4.10 (m, H—C(4')), 3.62 (m, 2 H—C (5')), 3.53 (m, CHCH₃), 2.48 (m H—C(2')), 2.21 (m, H—C (2')), 1.29 (d, CHCH₃), 1.24 (s, C(CH₃)₃. HRMS (FAB, M+H⁺) calculated for C₃₁H₃₆N₄O₁₀: 625.2509. Found: 625.2495. ESI-MS: 625 (M+H⁺), 647 (M+Na⁺), 1249 (2M+H⁺), 1271 (2M+Na⁺). R$_f$ (toluene/ethyl acetate 1:4) 0.50

Example 8

N6-((4-$^{tert}$butylphenoxy)acetyl)-3'-O-[2-(2-nitrophenyl)propoxycarbonyl]-2'-deoxyadenosine (13)

As described for 11 with N4-((4-$^{tert}$butylphenoxy)acetyl)-2'-deoxyadenosine (5) (2.73 g, 3.67 mmol) in 50 ml dichloromethane and 2 (1.31 g, 4.40 mmol) in 50 ml dichloromethane. Purification via flash chromatography (0–4% methanol in toluene/ethyl acetate (1.1)) yielded 2.05 g (86%) of the tile compound.

$^1$H-NMR (DMSO): δ_10.78 (br, NH), 8.66 (m, H—C(2), H—C(8)), 7.83 (m, 1H o ad NO₂), 7.70 (m, 1H m ad NO₂, 1Hp ad NO₂), 7.49 (m, 1H m ad NO₂), 7.30 (m, 2H o ad $^{tert}$butyl), 6.89 (m, 2H m ad $^{tert}$butyl), 6.43 (m, H—C(1')), 5,28 (m, H—C(3')), 5.14 (m, HO—C(5')), 4.98 (s, CH₂O), 4.34 (m, OCH₂CH), 4.12 (m, H—C(4')), 3.60 (m 2 H—C (5'), CHCH₃), 3.02 (m, H—C(2')), 2.57 (m, H—C(2')), 1.31 (d, CHCH₃), 1.24 (s, C(CH₃)₃). HRMS (FAB, M+H⁺) calculated for C₃₂H₃₆N₆O₉: 649.2621. Found: 649.2644. ESI-MS: 649 (M+H⁺), 671 (M+Na⁺), 1297 (2M+H⁺), 1319 (2M+Na⁺) (toluene/ethyl acetate 1:1) 0.17

Example 9

N2-((4-$^{tert}$butylphenoxy)acetyl)-3'-O-[2-(2-nitrophenyl)propoxycarbonyl]-2'-deoxyguanosine (14)

As described for 11 with N2-((4-$^{tert}$butylphenoxy)acetyl)-2'-deoxyguanosine (6) (5 g, 6.58 mmol) in 50 ml dichloromethane and 2 (2.57 g, 7.9 mmol) in 50 ml dichloromethane. Purification via flash chromatography (0–10% methanol in toluene/ethyl acetate (1:1) yielded 3.53 g (81%) of the title compound.

1H-NMR (DMSO): δ_11.74 (br, 2 NH), 8.23 (2s, H—C (8)), 7.83 (m, 1H o ad NO₂), 7.70 (m, 1H m ad NO₂, 1H p ad NO₂), 7.49 (m, 1H m ad NO₂), 7.30 (m, 2H o ad $^{tert}$butyl), 6.89 (m, 2H m ad $^{tert}$butyl), 6.18 (m, H—C(1')), 5.13 (m, H—C(3')), 5.06 (m, HO—C(5')), 4.81 (2s, CH₂O)), 4.34 (m, OCH₂CH), 4.04 (m, H—C(4')), 3.55 (m, 2 H—C(5'), CHCH₃), 2.83 (m, H—C(2')), 2.49 (m, H—C (2')), 1.29 (d, CHCH₃), 1.25 (s, C(CH₃)₃). HRMS (FAB, M+H⁺) calculated for C₃₂H₃₆N₆O₁₀: 665.2570. Found: 665.2582. ESI-MS: 665 (M+H⁺), 687 (M+Na⁺), 1329 (2M+H⁺), 1351 (2M+Na⁺). R$_f$(ethyl acetate/methanol 3:1) 0.18

Example 10

3'-O-[2-(2-nitrophenyl)propoxycarbonyl]thymidine-5'-O-[(2-cyanoethyl)-N,N-diisopropyl phosphoramidite] (15)

1.2 ml 2-cyanoethyl-N,N,N,N-tetraisopropylphosphorodiamidite (3.98 mmol) and 0.5 M pyridine hydrochloride (3.4 ml, 1.7 mmol) in acetonitrile are added to a solution of 1.53 g 3'-O-[2-(2-nitrophenyl)propoxycarbonyl]thymidine (11) (3.4 mmol) in 15 ml acetonitrile. After stirring for 1 hour, the reaction solution is diluted using dichloromethane (100 ml) and extracted with saturated NaHCO₃ (100 ml). The organic phase is washed with saturated NaCl (100 ml), dried via Na₂SO₄ and evaporated. Purification via flash chromatography (0–30% ethyl acetate in toluene) yielded 1.94 g (88%) of the title compound.

$^1$H-NMR (DMSO): δ_11.26 (br, NH), 7.82 (m, 1H o ad NO₂), 7.69 (m, 1H m ad NO₂, 1H p ad NO₂), 7.47–7.55 (m, H—C(5), 1H m ad NO₂), 6.08 (m, H—C(1')), 5.09 (m, H—C(3')), 4.27–4.35 (m, OCH₂CH₂), 4.12 (m, H—C(4')), 3.70–3.83 (m 2 H—C(5'), OCH₂CH₂CN), 3.49–3.59 (m, 3 CHCH₃), 2.75 (m, CH₂CH₂CN), 2.29 (m, 2 H—C(2')), 1.78 (m, CH₃), 1.28 (d, CH₃), 1.09–1.24 (m, 7 CH₃).

$^{31}$P-NMR (DMSO): δ_149.36, 149.33, 149.29 ESI-MS: 649 (M+H⁺), 672 (M+Na⁺), 1321 (2M+Na⁺). HRMS (FAB, M+H⁺) calculated for C₂₉H₄₀N₅O₁₀P: 650.2590. Found: 650.2576. R$_f$(toluene/ethyl acetate 1:1) 0.37

Example 11

N4-((4-$^{tert}$butylphenoxy)acetyl)-3'-O-[2-(2-nitrophenyl)propoxycarbonyl]-2'-deoxycytidine-5'-O-[(2-cyanoethyl)-N,N-diisopropyl phosphoramidite] (16)

As described for 15 with N4-((4-$^{tert}$butylphenoxy)acetyl)-3'-O-[2-(2-nitrophenyl)propoxycarbonyl]-2'-deoxycytidine (12) (1.51 g, 2.41 mmol), 2-cyanoethyl-N,N,N,N-tetraisopropyl-phosphordiamidite (0.9 ml, 2.84 mmol) and 0.5 M pyridine hydrochloride (2.6 ml, 1.3 mmol). Purification via flash chromatography (0–30% ethyl acetate in toluene) yielded 1.61 g (81%) of the title compound.

1H-NMR (DMSO): δ_10.90 (br, NH), 8.14 (m, H—C (6)), 7.82 (m, 1H o ad NO₂), 7.69 (m, 1H m ad NO₂, 1H p ad NO₂), 7.48 (m, 1H m ad NO₂), 7.29 (m, 2H o ad $^{tert}$butyl), 7.14 (m, H—C(5)), 6.83 (m, 2H m ad $^{tert}$butyl), 6.07 (m, H—C(1')), 5.10 (m, H—C(3')), 4.77 (s, OCH₂), 4.30 (m, OCH₂CH₂, H—C(4')), 3.75 (m, 2 H—C(5'), OCH₂CH₂CN), 3.55 (m, 3 CHCH₃), 2.73 (m, CH₂CH₂CN), 2.55 (m, H—C(2')), 2.25 (m, H—C(2')), 1.29 (m, CH₃), 1.15 (m, 7 CH$_3$). $^{31}$P-NMR (DMSO): δ_149.35. HRMS (FAB, M+H$^+$calculated for C$_{40}$H$_{53}$N$_6$O$_{11}$P: 825.3587. Found: 825.3568. ESI-MS: 825 (M+H$^+$), 847 (M+Na$^+$), 1649 (2M+H$^+$), 1671 (2M+Na$^+$). R$_f$(toluene/ethyl acetate 1:1) 0.43

Example 12

N6-((4-$^{tert}$butylphenoxy)acetyl)-3'-O-[2-(2-nitrophenyl)propoxycarbonyl]-2'-deoxyadnosine-5'-O-[(2-cyano-ethyl)-N,N-diisopropylphosphoramidite] (17)

As described for 15 with N6-((4-$^{tert}$butylphenoxy)acetyl)-3'-O-[2-(2-nitrophenyl)propoxycarbonyl]-2'-deoxyadenosine (13) (1.90 g, 2.93 mmol), 2-cyanoethyl-N,N,N,N-tetraisopropyl-phosphordiamidite (1.2 ml, 3.78 mmol) and 0.5 M pyridine hydrochloride (2.9 ml, 1.45 mmol). Purification via flash chromatography (0–30% ethyl acetate in toluene) yielded 1.9 g (65%) of the title compound.

$^1$H-NMR (DMSO): δ_11.70 (br, NH), 8.64 (m, H—C(2)), H—C(8)), 7.83 (m, 1H o ad NO$_2$), 7.71 (m, 1H m ad NO$_2$, 1H p ad NO$_2$), 7.48 (m, 1H m ad NO$_2$), 7.29 (m, 2H o ad $^{tert}$butyl), 6.88 (m, 2H m ad $^{tert}$butyl), 6.45 (m, H—C(1')), 5.33 (m, H—C(3')), 4.98 (s, OCH$_2$), 4.36 (m, OCH$_2$CH$_2$, 4.24 (m, H—C(4')), 4.78 (m, 2 H—C(5'), OCH$_2$CH$_2$CN), 3.53 (m, 3 CHCH$_3$), 3.12 (m, H—C(2')), 2.74 (m, CH$_2$CH$_2$CN), 2.60 (m, H—C(2')), 1.30 (d, CH$_3$), 1.11 (m, 7 CH$_3$). $^{31}$P-NMR (DMSO): δ_149.24, 149.20, 149.16. HRMS (FAB, M+H$^+$) calculated for C$_{41}$H$_{53}$N$_8$O$_{10}$P: 849.3700. Found: 849.3723. ESI-MS: 849 (M+H$^+$), 871 (M+Na$^+$), 1697 (2M+H$^+$), 1719, 2M+Na$^+$). R$_f$(toluene/ethyl acetate 1:1) 0.53

Example 13

N2-((4-$^{tert}$butylphenoxy)acetyl)-3'-O-[2-(2-nitrophenyl)propoxycarbonyl]-2'-deoxyguanosine-5'-O-[(2-cyanoethyl)-N,N-diisopropylphosphoramidite] (18)

As described for 15 with N2-((4-$^{tert}$butylphenoxy)acetyl)-3'-O-[2-(2-nitrophenyl)propoxycarbonyl]-2'-deoxyguanosine (14) (1.0 g, 1.50 mmol), 2-cyanoethyl-N,N,N,N-tetraisopropyl-phosphordiamidite (0.9 ml, 2.84 mmol) and 0.5 M pyridine hydrochloride (1.75 ml, 0.87 mmol). Purification via flash chromatography (33–66% acetone in petroleum ether) yielded 1.19 g(91%) of the title compound.

$^1$H-NMR (DMSO): δ_11.45 (br, 2 NH), 8.15 (m, H—C(8)), 7.83 (m, 1H o ad NO$_2$), 7.70 (m, 1Hm ad NO$_2$, 1H p ad NO$_2$), 7.49 (m, 1H m ad NO$_2$), 7.29 (m, 2H o ad $^{tert}$butyl), 6.88 (m, 2H m ad $^{tert}$butyl), 6.19 (m, H—C(1')), 5.23 (m, H—C(3')), 4.79 (m, OCH$_2$), 4.36 (m, OCH$_2$CH$_2$), 4.20 (m, H—C(4')), 3.73 (m, 2 H—C(5'),OCH$_2$CH$_2$CN), 3.55 (m, 3 CHCH$_3$), 2.87 (m, CH$_2$CH$_2$CN), 2.76 (m, H—C(2')), 2.57 (m, H—C(2')), 1.30 (d, CH$_3$), 1.15 (m, 7 CH$_3$). $^{31}$P-NMR (DMSO): δ_149.46, 149.41 HRMS (FAB, M+H$^+$calculated for C$_{41}$H$_{53}$N$_8$O$_{11}$P: 865.3649. Found: 865.3660 ESI-MS: 865 (M+H$^+$), 887 (M+Na$^+$), 1751 (2M+Na$^+$). R$_f$ (toluene/ethyl acetate/methanol 5:4:1) 0.39

Example 14

N-methyl-N3-[(6-nitroveratryl)oxycarbonyl] imidazolium chloride (19) 2 g chloroformic acid-6-nitroveratryl ester (7.25 mmol; company of Fluka, Ulm) are added at 0° C. to 1.44 ml N-methylimidazole (18.1 mmol) and molecular sieve 4 Å in 100 ml absolute dichloromethane. The reaction solution is stirred at 0° C. for 15 minutes. This reaction solution is used directly for acylations.

Example 15

3'-O-[(6-nitroveratryl)oxycarbonyl]thymidine (21)

A solution of 1.97 g 5'-O-(4,4'-dimethoxytrityl)thymidine (3.62 mmol) in 18 ml absolute dichloromethane and 2 ml absolute pyridine is added in a nitrogen atomsphere and in the absence of light to an N-methyl-N3-[(6-nitroveratryl) oxycarbonyl]imidazoliumchloride acylation reaction (19) (produced from 7.25 mmol chloroformic acid-6-nitroveratryl ester). The reaction mixture is stirred in the dark at 4° C. overnight. The molecular sieve is separated and the organic phase is extracted twice against saturated NaHCO$_3$ (100 ml). After drying via Na$_2$SO$_4$, 200 ml of a 10% trichloroacetic acid in dichloroethane are added to the organic phase and stirred at room temperature for 5 minutes. The deep-red solution is extracted twice with saturated NaHCO$_3$ (200 ml), the organic phase is dried via Na$_2$SO$_4$ and evaporated. Purification via flash chromatography (66–80% ethyl acetate in toluene) yielded 1.153 g of the title compound (66% yield)

Example 16

3'-O-[(6-nitroveratryl)oxycarbonyl]thymidine-5'-O-[(2-cyanoethyl)-N,N-diisopropylphospboramidite] (22)

1 g 3'-O-[(6-nitroveratryl)oxycarbonyl]thymidine (21) (2.08 mmol) are dissolved in a nitrogen atomsphere in 20 ml absolute dichloromethane. 0.22 ml N-methylmorpholine (2 mmol) and 0.24 ml 2-cyanoethyl-N,N-diisopropylphosphorimidochloridite (1.1 mmol) are added in a nitrogen atmosphere and in the absence of light. Having stirred for 1 hour, extraction is carried out against saturated NaHCO$_3$ (200 ml) and then against saturated NaCl (200 ml), the organic phase is dried via Na$_2$SO$_4$ and evaporated. Purification via flash chromatography (50–66% ethyl acetate in toluene), yielded 0.74 g of the title compound (55% yield).

Example 17

Production of DNA chips by means of monomeric building blocks of the type 3'-O-[2-(2-nitrophenyl) propoxycarbonyl]-5'-phosphoramidite The DNA chip synthesis was carried out analogously to the method by Fodor et al. (Science 1991, 251, p. 767 et seq.) on a glass surface as a support using masks or no masks, as already described in German patent applications DE 198 58 440.7 or DE 199 62 803.3.

Figure 8:
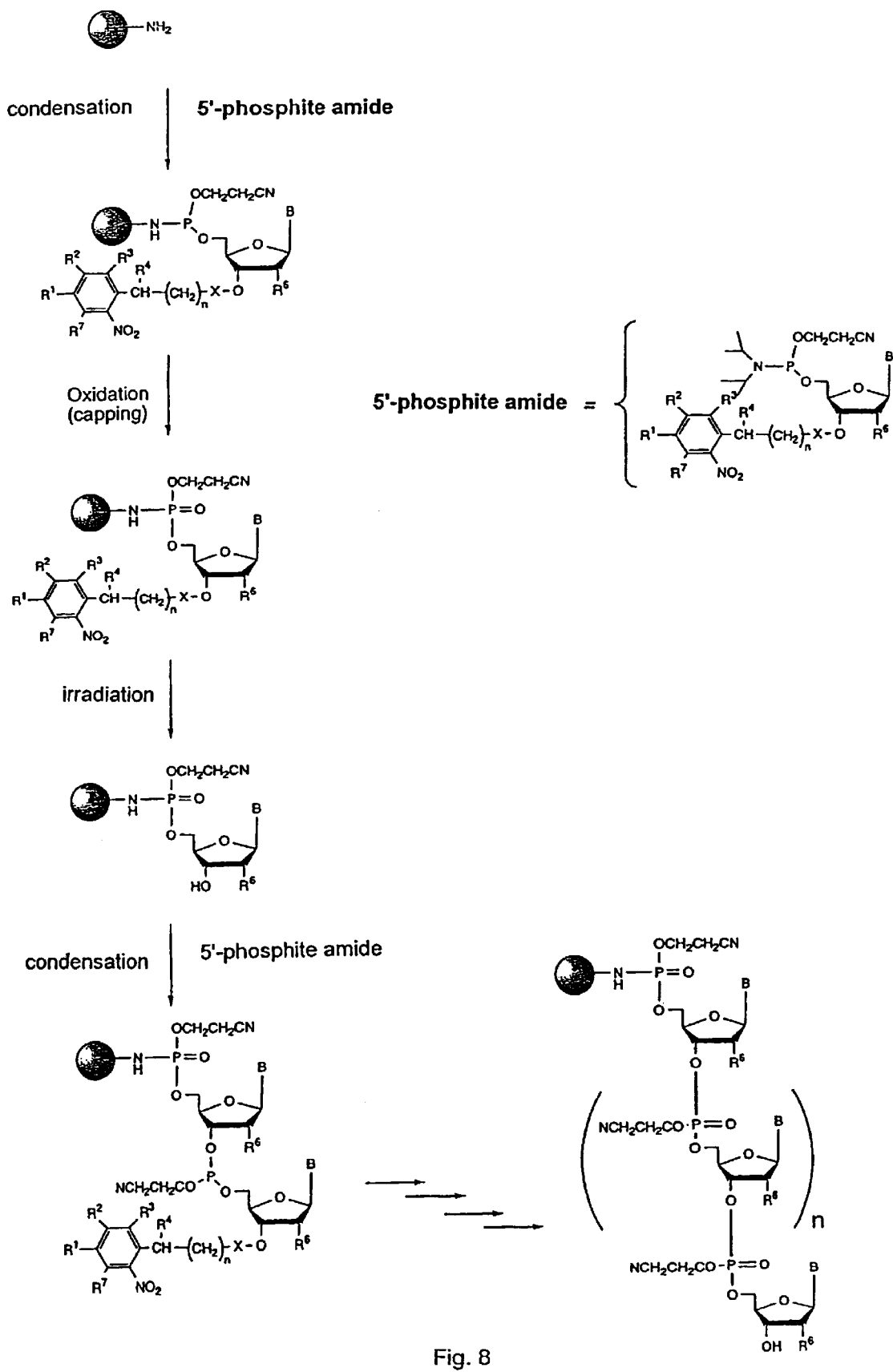
FIG. 8: synthesis of an oligonucleotide using 3'-O-photolabile 5'-phosphite amides according to formula (I)

The irradiation carried out for abstracting the 3'-O-[2-(2-nitrophenyl)propoxycarbonyl] group is appropriately made using a base during the irradiation. In this connection, reference is made to German patent application DE 198 58 440.7. The reaction course is shown in FIG. 8 by way of diagram. The compound 3'-O-[(2-(2-nitrophenyl) propoxycarbonyl]thymidine-5'-O-[(cyanoethyl)-N,N-diisopropyl phosphoramidite] according to the invention was used as monomeric building blocks. In this connection, reference is made to German patent application DE 199 15 867.3. The applied cycle and the special synthesis conditions are described in German patent application DE 198 58 440.7, to which reference is made herein. The nucleotide strand is linked to the solid support phase via the 5' end. Thus, the 3'-OH end is freely available after concluding the synthesis and finally cleaving the protective group. As a result, enzyme reactions which call for a free 3' end (polymerase reactions, ligase reactions, PCR, cDNA synthesis, sequencing, . . . ) can be carried out with these bio chips.

Figure 9:
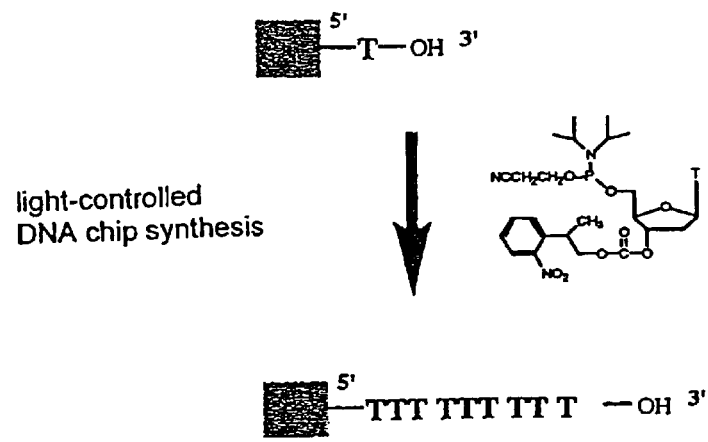
FIG. 9: fluorescence image of a DNA chip produced using 3'-O-[2-(2-nitrophenyl)propoxycarbonyl]-thymidine-5'-O-[(2-cyanoethyl)-N,N-diisopropylphosporamidite]. The sequence $dT_9$ was built up on the support surface. The $dT_9$ oligonucleotide is anchored with its 5' end on the surface, and 3'-OH is freely available for an enzyme reaction. The illustrated fluorescence image was obtained after hybridizing the chip with Cy5-labeled $dA_{16}$ (SEQ. ID NO: 1). The pattern corresponds to the mask used.
Figure 9:
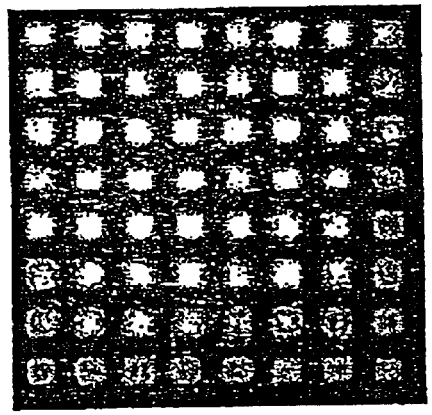

FIG. 9 shows the fluorescence image of the produced chip with d(T$_9$) after hybridization with Cy5-labeled d(A$_{16}$). The pattern corresponds to the mask applied, i.e. a successful DNA chip synthesis was possible.

Example 18

Production of DNA chips by means of monomeric building blocks of the type 3'-O-[(6-nitroveratryl) oxycarbonyl-5'-phosphoramidite The DNA chip synthesis was carried out on a glass surface as support analogously to the method by Fodor et al. (Science 1991, 251, p. 767 et seq.) using masks or no masks, as already described in German patent applications DE 198 58 440.7 or DE 199 62 803.3.

The irradiation serving for abstracting the 3'-O-(6-nitroveratyl) group is appropriately made without adding solvents, i.e. "in a dry state". The compound 3'-O-[(6-nitroveratyl)oxycarbonyl]thynidine-5'-O-[(2-cyanoethyl)-N,N-diisopropylphosphoramidite according to the invention is used as monomeric building block. In this connection, attention is directed to German patent application DE 100 03 631.7 to which reference is mnade herein. The nucleotide strand is linked via the 5' end to the solid support phase. Thus, the 3'-OH end is freely available after concluding the synthesis and finally cleaving the protective group. As a result, enzyme reactions which call for a free 3' end (polymerase reactions, ligase reactions, PCR, cDNA synthesis, sequencing, . . . ) can be carried out with these biochips.

Figure 10:
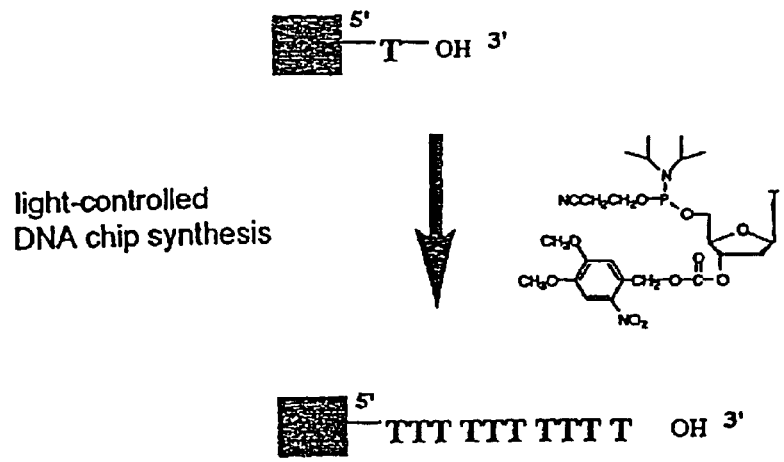
FIG. 10: Fluorescence image of a DNA chip which was produced using 3'-O -[6-nitroveratryl)oxycarbonyl] thymidine-5'-O-[(2-cyanoethyl)-N,N-diisopropyl-phosohormidite]. The sequence $dT_{10}$(SEQ ID NO: 2) was built up on the support surface. The $dT_{10}$ oligonucleotide is anchored with its 5' end on the surface, and 3'-OH is freely available for an enzyme reaction. The illustrated fluorescence image was obtained after hybridizing the chip with Cy5-labeled dA16. The pattern corresponds to the mask used.
Figure 10:
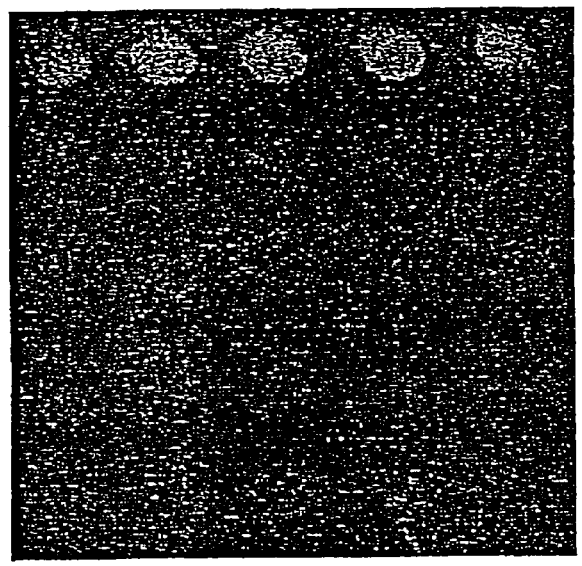
Figure 11:
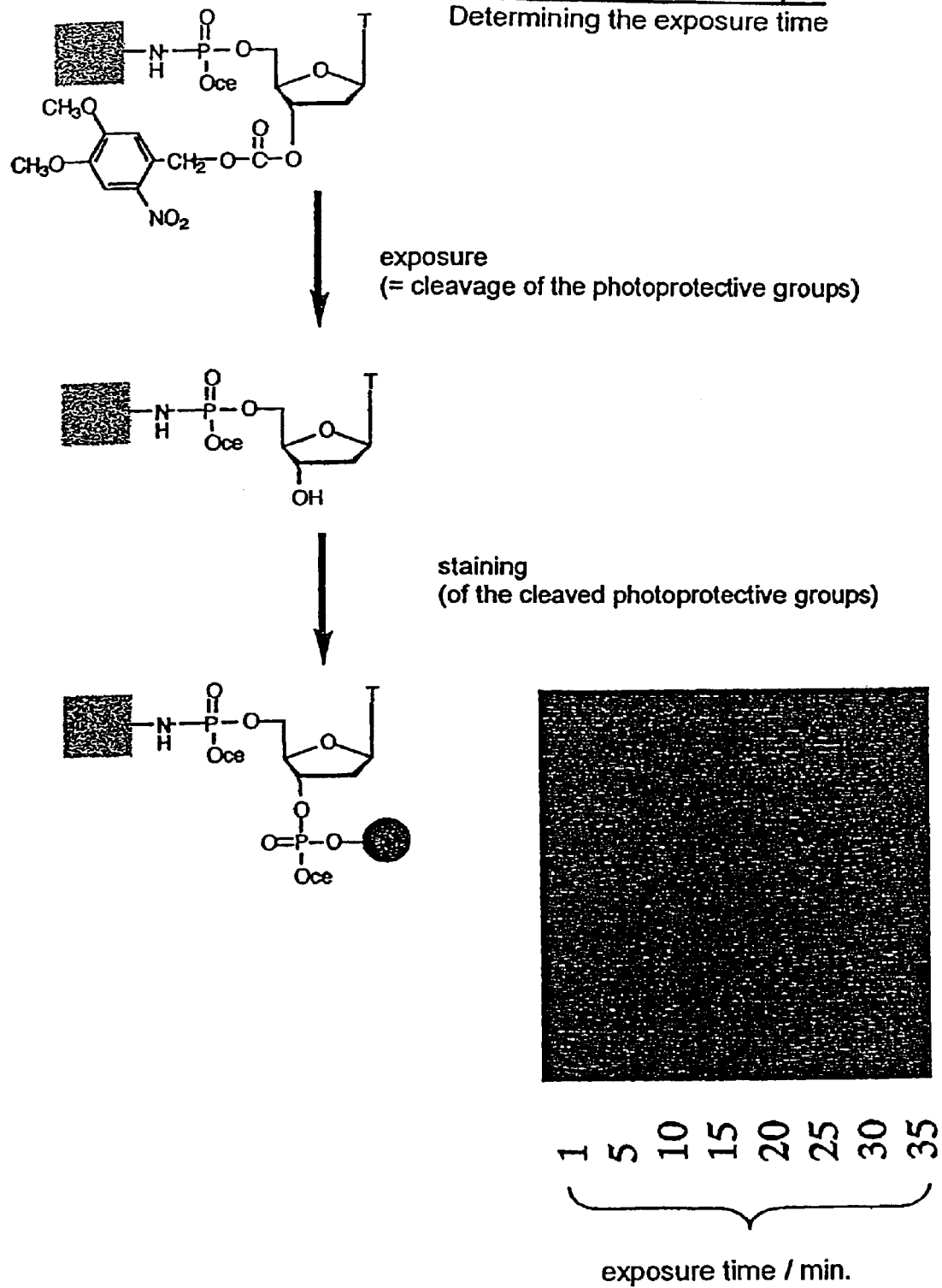
FIG. 11 shows the fluorescence image of a DNA chip which was used for determining the irradiation period for the 3'-O-[6-nitroveratryl)oxycarbonyl] protective group. A surface-bound 3'-O-[(6-nitroveratryl)oxycarbonyl] building block was irradiated from left to right for 1, 5, 10, 15, 20, 25, 30, and 35 minutes. Thereafter, the resultant abstraction of the 3'-O-[(6-nitroveratryl)oxycarbonyl] groups was made visible by permanent labeling using a Cy5 dye. The pattern corresponds to the mask used.

FIG. 10 shows the fluorescence image of the chip produced with $d(T_{10})$ after hybridization with Cy5-labeled $d(A_{16})$. The pattern corresponds to the applied mask, i.e. a successful DNA chip synthesis was possible.

Example 19

Completion of a polymerase chain reaction (primer extension) on a DNA chip which was produced by means of monomeric building blocks of the type 3'-O-[2-(2-nitrophenyl)propoxycaronyl]thymidine-5'-O-[(2-cyanoethyl)-N,N-diisopropyl phosphoramidite A 25 µl reaction chamber (EasiSeal, Hybaid) is fixed over the array on the $dT_9$ DNA chip for carrying out the enzyme reaction.

1 µl of the template (d(CTATAGTGAGTCGTATT AAAAAAAAAA), SEQ ID NO: 9, 100 µM) is denatured in 9.5 µl of autoclaved water at 95° C. for 5 minutes and filled into the reaction chamber after 3 minutes on ice. 12.5 µl of the buffer (20 mM TrisHCl, pH 7.5, 10 mM $MgCl_2$, 15 mM DTT), 1 µl dNTP-Mix (10 mM) and finally 1 µl of the Klenow fragment (3'exo+5'exo; 5000 U/ml); New England Biolabs) are also added. After careful mixing, the reaction chamber is closed and the reaction is carried out at 37° C. overnight.

For the purpose of detection, washing is subsequently carried out at 95° C. for 30 seconds using stripping buffer (2.5 mM $Na_2HPO_4$, 0.1% (v/v) SDS) and then hybridization is effected with 5'-Cy5-dA16 and 5'-Cy3-d (CTATAGTGAGTCGTATT), SEQ ID NO: 10.

Example 20

Completion of a ligase reaction on a DNA chip produced by means of monomeric building blocks of the type 3'-O-[2-(2-nitrophenyl)propoxycarbonyl] thymidine-5'-O-[(2-cyanoethyl)-N,N-diisopropyl phosphoramidite]

A 25 µl reaction chamber (EasiSeal, Hybaid) is fixed over the array on the $dT_{10}$DNA chip for carrying out the enzyme reaction.

1 µl of the template (d(CTATAGTGAGTCGTATTAAAAAAAAAA), SEQ ID NO: 9, 100 µM) is filled into the reaction chamber in 17.8 µl autoclaved water. After 2 minutes, 1µl d(5'-phosphate-AATACGACTCAC SEQ ID NO: 7, [100 µM] is added. After another 2 minutes, 5 µl of the ligase buffer (5×; 250 mM TrisHCl, pH 7.5, 50 mM $MgCl_2$, 50 mM DTT, 5 mM ATP, 125 µg BSA/ml) and finally 0.2 µl of the T4-DNA ligase (400 00 U/ml; New England Biolabs) are also added. The reaction chamber is closed and the reaction is carried out at 16° C. for 1 hour.

For the purpose of detection, washing is subsequently carried out at 95° C. for 30 seconds using stripping buffer (2.5 mM $Na_2HPO_4$, 0.1% (v/v) SDS) and then hybridization is effected by means of 5'-Cy5 dA16 and 5'-Cy3-d (CTATAGTGAGTCGTATT), SEQ ID NO: 10.

---

What is claimed is:

1. Nucleoside derivatives having photolabile protective group of general formula (I).

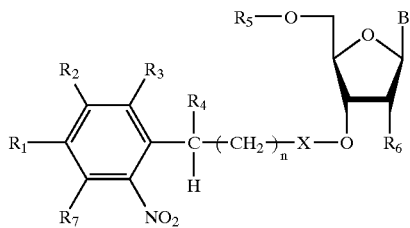

in which $R^1$=H, $NO_2$, CN, $OCH_3$, halogen, an alkyl, alkoxy or alkoxyalkyl residue having 1 to 4 C atoms or an optionally substituted aryl residue or an aliphatic acyl residue having 2 to 5 atoms, $R^2$=H, $NO_2$, CN, $OCH_3$, halogen, an alkyl, alkoxy or alkoxyalkyl residue having 1 to 4 C atoms or an optionally substituted aryl residue or an aliphatic acyl residue 2 to 5 atoms, $R^3$=H, halogen, $NO_2$, CN, $OCH_3$, an alkyl, alkoxy or alkoxyalkyl residue having 1 to 4 C atoms or an optionally substituted aryl residue or aliphatic acyl residue having 2 to 5 C atoms, $R^4$=H, halogen, $NO_2$, CN, $OCH_3$, an alkyl, alkoxy, or alkoxyalkyl residue having 1 to 4 C atoms or an optionally substituted aryl residue or aliphatic acyl residue having 2 to 5 atoms, $R^5$=H, dimethoxytrityl or a protective group common in the chemistry of nucleotides or a functional group common for the production of oligonucleotides, $R^6$=H, OH, halogen or $\Psi R^8$, wherein $\Psi$=O or S and $R^8$=alkyl or alkoxyalkyl having 1 to 4 C atoms or an optionally substituted aryl residue or an aliphatic acyl residue having 2 to 5 atoms and a protective group common in the chemistry of nucleotides, $R^7$=H, $NO_2$, CN, $OCH_3$, halogen, an alkyl, alkoxy or alkoxyalkyl residue having 1 to 4 C atoms or an optionally substituted aryl residue or aliphatic acyl residue having 2 to 5 atoms, n=0 or 1, X=$SO_2$, OC(O), OC(S) with the proviso that in case X=O—C(O) n≠0, B=H, adenine, cytosine, guanine, thymine, uracil, 2,6-diaminopurine-9-yl, hypoxanthine-9-yl, 5-methylcytosine-1-yl, 5-amino-4imidazole carboxylic acid-1-yl or 5-amino-4-imadazole carboxylic acid amide-3-yl, wherein in case B=adenine, cytosine or guanine the primary amino function optionally has a temporary or permanent protective group and/or thymine or uracil optionally has a permanent protective group at the O4 position.

2. The nucleoside derivative according to claim 1, provided when $R^4 \neq H$, $R^1$, $R^2$ and $R^3$ are H each. (see second preliminary amendment).

3. The nucleoside derivative according to claim 1, provided when $R^2$=$OCH_3$, $R^3$=H.

4. The nucleoside derivative according to any of claims 1 to 3, wherein $R^4$=$CH_3$.

5. The nucleoside derivative according to claim 1, wherein for the production of oligonucleotides the common functional group at the $R^5$ position is a phosphite amide group of the formula

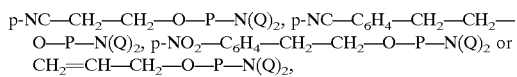

wherein the Q groups may be equal or different and represent linear or branched alkyl residues having 1 to 4 C atoms.

6. The nucleoside derivative according to claim 5, wherein the Q group is ethyl or isopropyl.

7. The nucleoside derivative according to claim 1, wherein the residue $R^8$ in the group $\Psi R^8$ at the $R^6$ position is an O-alkyl, O-alkenyl, O-acetal or O-silyl ether group if $\Psi$=O or an O-alkyl group if $\Psi$=S.

8. The nucleoside derivative according to claim 7, wherein halogen is Cl, Br, or I.

* * * * *

SEQUENCE LISTING

```
<160> NUMBER OF SEQ ID NOS: 10

<210> SEQ ID NO 1
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 1
aaaaaaaaaa aaaaaa                                                    16

<210> SEQ ID NO 2
<211> LENGTH: 10
<212> TYPE: DNA
<213> ORGANISM: Artificial Sequence
```

```
<220> FEATURE:
<223> OTHER INFORMATION: Synthetic Oligonucleotide

<400> SEQUENCE: 2
tttttttttt                                                            10

<210> SEQ ID NO 3
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 3
ctatagtgag tcgta                                                      15

<210> SEQ ID NO 4
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 4
aaaaaaaaaa ttatgctgag tgatatc                                         27

<210> SEQ ID NO 5
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 5 tttttttta atacgactca ctatag                                           26

<210> SEQ ID NO 6
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 6
ctatagtgag tcgtatta                                                   18

<210> SEQ ID NO 7
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 7
aatacgactc actatag                                                    17

<210> SEQ ID NO 8
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 8
tttttttttt aatacgactc actatag                                         27
```

```
<210> SEQ ID NO 9
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 9
ctatagtgag tcgtattaaa aaaaaaa                                    27

<210> SEQ ID NO 10
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 10
ctatagtgag tcgtatt                                               17
```